(12) United States Patent
Sudol

(10) Patent No.: US 12,303,333 B2
(45) Date of Patent: May 20, 2025

(54) ELECTRICAL WIRE CONNECTION IN INTRALUMINAL ULTRASOUND IMAGING DEVICES AND SYSTEM

(71) Applicant: KONINKLIJKE PHILIPS N.V., Eindhoven (NL)

(72) Inventor: Wojtek Sudol, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 163 days.

(21) Appl. No.: 17/793,082

(22) PCT Filed: Jan. 5, 2021

(86) PCT No.: PCT/EP2021/050031
§ 371 (c)(1),
(2) Date: Jul. 15, 2022

(87) PCT Pub. No.: WO2021/144160
PCT Pub. Date: Jul. 22, 2021

(65) Prior Publication Data
US 2023/0052311 A1    Feb. 16, 2023

Related U.S. Application Data

(60) Provisional application No. 62/961,883, filed on Jan. 16, 2020.

(51) Int. Cl.
*A61B 8/00*    (2006.01)
*A61B 8/08*    (2006.01)
*A61B 8/12*    (2006.01)

(52) U.S. Cl.
CPC ............ *A61B 8/445* (2013.01); *A61B 8/0883* (2013.01); *A61B 8/12* (2013.01); *A61B 8/4488* (2013.01); *A61B 8/56* (2013.01); *A61B 2562/182* (2013.01)

(58) Field of Classification Search
CPC ......... A61B 8/445; A61B 8/0883; A61B 8/12; A61B 8/4488; A61B 8/56; A61B 2562/182
See application file for complete search history.

(56) References Cited

U.S. PATENT DOCUMENTS 4,993,968 A * 2/1991 Guletsky ............. H01R 9/05
439/942
5,947,905 A    9/1999 Hadjicostis
(Continued)

FOREIGN PATENT DOCUMENTS

| JP | 4985129 B2 * | 7/2012 | ............ H01L 24/83 |
| WO | 2017013745 A1 | 1/2017 | |
| WO | 2018060061 A1 | 4/2018 | |

OTHER PUBLICATIONS

International Search Report and Written Opinion of PCT/EP2021/050031, dated Apr. 21, 2021.

*Primary Examiner* — Chao Sheng

(57) ABSTRACT

An intraluminal imaging device includes a flexible elongate member configured to be positioned within a body lumen of a patient. The flexible elongate member includes a plurality of coaxial cables. Each of the plurality of coaxial cables includes a conductive shield layer. The intraluminal imaging device also includes an ultrasound imaging assembly positioned at a distal portion of the flexible elongate member and in communication with the plurality of coaxial cables. The ultrasound imaging assembly includes a transducer array configured to obtain ultrasound data and a conductive pad. The conductive shield layer of each of the plurality of coaxial cables is mechanically and electrically coupled to the conductive pad. Associated devices, systems, and methods are also provided.

16 Claims, 17 Drawing Sheets

(56) References Cited

U.S. PATENT DOCUMENTS

| | | |
|---|---|---|
| 6,497,667 B1 | 12/2002 | Miller et al. |
| 8,792,962 B2 | 7/2014 | Esguerra |
| 10,041,851 B2 | 8/2018 | Doering |
| 2013/0267853 A1* | 10/2013 | Dausch ................ A61B 8/4494 |
| | | 600/459 |
| 2014/0276224 A1 | 9/2014 | Ranganathan |
| 2017/0194744 A1* | 7/2017 | Guetig ............... H01R 13/6474 |
| 2017/0326589 A1 | 11/2017 | Sudol |
| 2019/0208621 A1* | 7/2019 | Lo .......................... H05K 1/181 |

* cited by examiner

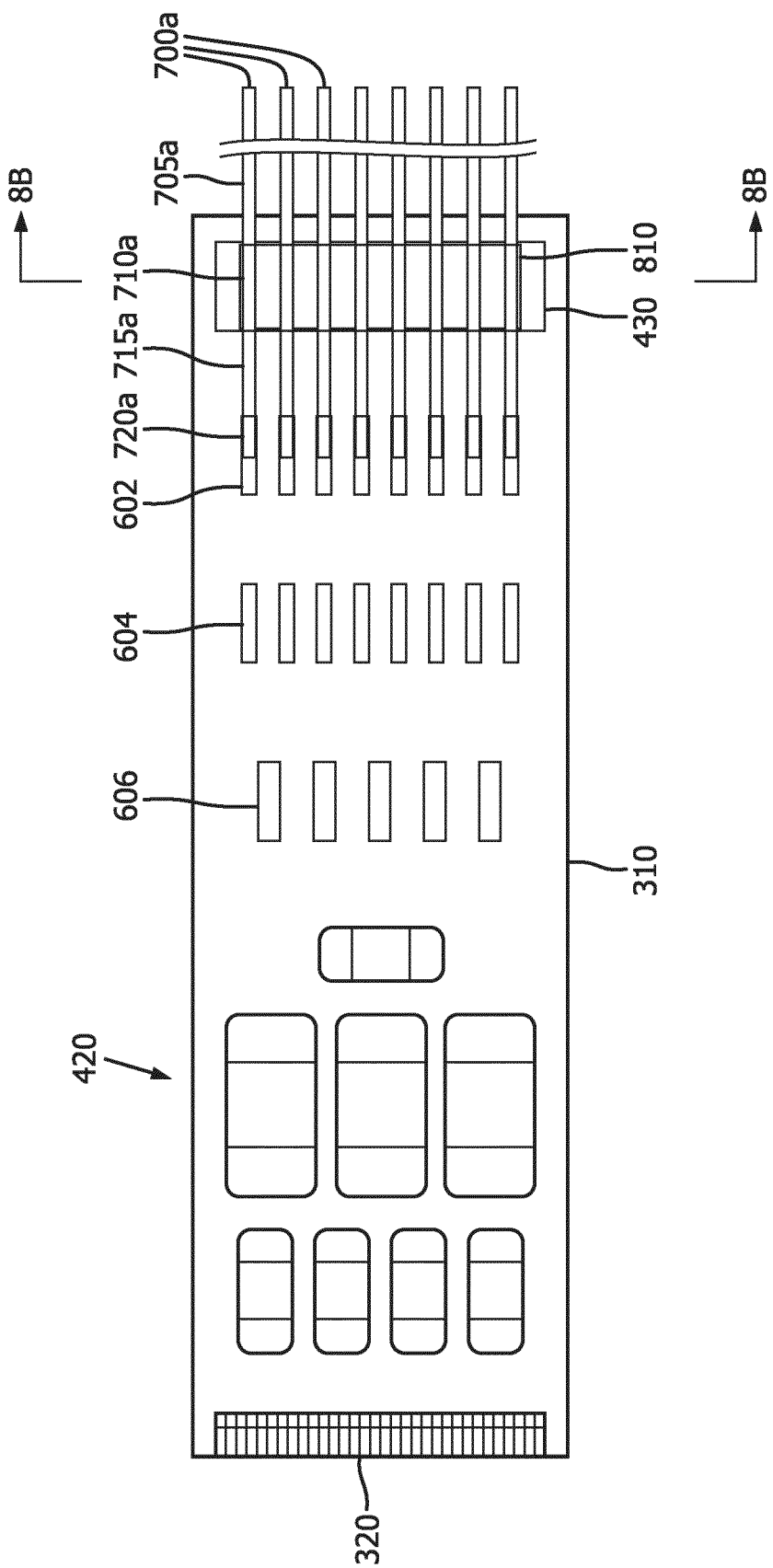

ELECTRICAL WIRE CONNECTION IN INTRALUMINAL ULTRASOUND IMAGING DEVICES AND SYSTEM

TECHNICAL FIELD

The present disclosure relates generally to ultrasound imaging systems, and in particular, to electrical wire connections for imaging catheters, such as intra-cardiac echocardiography (ICE) catheters.

BACKGROUND

Diagnostic and therapeutic ultrasound catheters have been designed for use inside many areas of the human body. In the cardiovascular system, a common diagnostic ultrasound method is intraluminal ultrasound imaging with intra-cardiac echocardiography (ICE) being a specific example of intraluminal imaging. Typically, a single rotating transducer or an array of transducer elements is used to transmit ultrasound at the tips of the catheters. The same transducers are used to receive echoes from the tissue. A signal generated from the echoes is transferred to a console which allows for the processing, storing, display, or manipulation of the ultrasound-related data.

Intraluminal imaging catheters, such as ICE catheters (e.g., Siemens Acunav, St. Jude ViewFlex), are generally used to image heart and surrounding structures, for example, to guide and facilitate medical procedures, such as transseptal lumen punctures, left atrial appendage closures, atrial fibrillation ablation, and valve repairs. Commercially-available ICE catheters have distal ends which can be articulated by a steering mechanism located in a handle at the proximal end of the catheter. For example, an intraluminal imaging catheter such as an ICE catheter may be inserted through the femoral or jugular vein when accessing the anatomy and steered in the heart to acquire images necessary to the safety of the medical procedures.

ICE catheters must meet national and/or international requirements that stipulate a distal tip of a catheter must not separate when tensile pull loads of various magnitudes are applied depending primarily on the diameter of the catheter. This ensures that the catheter can be safely removed from a patient's body without a breakage causing the tip to be left within the heart or vasculature. Because ICE catheters are necessarily extremely narrow and the distal catheter assembly houses many transducers, circuits, and other electrical components, achieving the necessary tensile strength in an extremely confined space is difficult.

SUMMARY

Embodiments of the present disclosure are directed to electrical wire connections for imaging catheters, such as intra-cardiac echocardiography (ICE) catheters. There is a need for a simple, compact, stronger method and apparatus to connect the ultrasound imaging assembly of an ICE catheter to the elongate wires that carry it. To achieve a stronger mechanical coupling, a mass of solder can be applied to form a mechanical and electrical bond between the shield layers of a number of coaxial cables and a grounding pad positioned on an interposer within an ultrasound imaging assembly. The center conductors of these coaxial cables may be bonded to corresponding conductive pads elsewhere on the interposer and may provide signal communication between the ultrasound imaging assembly and a computer. Single conductor cables may be connected to the interposer at other places within the ultrasound imaging assembly. The bonding of shield layers of coaxial cables to a grounding pad on the interposer provides a common ground signal relative to all center conductor signals of the coaxial cables and provides a strong physical connection between the catheter cables and the ultrasound imaging assembly making it easier to achieve the necessary tensile strength of intra-cardiac echocardiography (ICE) catheters.

According to an exemplary aspect of the present disclosure, an intraluminal imaging device is provided. The intraluminal imaging device comprises a flexible elongate member configured to be positioned within a body lumen of a patient, the flexible elongate member comprising a plurality of coaxial cables, wherein each of the plurality of coaxial cables comprises a conductive shield layer; and an ultrasound imaging assembly positioned at a distal portion of the flexible elongate member and in communication with the plurality of coaxial cables, the ultrasound imaging assembly comprising: a transducer array configured to obtain ultrasound data; and a first conductive pad, wherein the conductive shield layer of each of the plurality of coaxial cables is mechanically and electrically coupled to the first conductive pad.

In some aspects, the intraluminal imaging device further comprises: a solder mass positioned over the first conductive pad, wherein the conductive shield layer of each of the plurality of coaxial cables is mechanically and electrically coupled to the first conductive pad and to one another via the solder mass. In some aspects, the solder mass is positioned around a perimeter of the plurality of coaxial cables. In some aspects, the solder mass is configured to support a tensile load of at least 15 N. In some aspects, each of the plurality of coaxial cables comprises an insulating jacket around the conductive shield layer, the conductive shield layer comprises an exposed portion without the insulating jacket, and corresponding dimensions of the exposed portion of the conductive shield layer and the first conductive pad are equal. In some aspects, each of the plurality of coaxial cables comprises a center conductor and an insulation layer around the center conductor, the conductive shield layer is positioned around the insulation layer, and the solder mass is positioned between the conductive shield layer and the insulation layer. In some aspects, the plurality of coaxial cables comprises a first row of coaxial cables and a second row of coaxial cables, the first row of coaxial cables is positioned over the first conductive pad, and the second row is positioned over the first row of coaxial cables. In some aspects, the solder mass is positioned between the first row of coaxial cables and the second row of coaxial cables. In some aspects, each of the plurality of coaxial cables is spaced apart, wherein the solder mass is positioned between each of the plurality of coaxial cables. In some aspects, the first conductive pad comprises an electrical ground for the plurality of coaxial cables. In some aspects, each of the plurality of coaxial cables comprises a center conductor, wherein the ultrasound imaging assembly comprises a plurality of second conductive pads, the center conductor of each of the plurality of coaxial cables is mechanically and electrically coupled to a corresponding one of the plurality of second conductive pads, and the center conductor is configured to carry electrical signals to and from the ultrasound imaging assembly. In some aspects, the flexible elongate member comprises a plurality of single conductor cables positioned over the plurality of coaxial cables, the ultrasound imaging assembly comprises a plurality of third conductive pads configured to be mechanically and electrically coupled to the plurality of single conductor cables, and the plurality of single conductor cables are configured to carry the electrical signals to and from the ultrasound imaging assembly. In some aspects, the flexible elongate member comprises a catheter configured to be positioned within a heart of the patient. In some aspects, the ultrasound imaging assembly further comprises a circuit board in communication with the transducer array, the first conductive pad positioned on a surface of the circuit board.

According to an exemplary aspect of the present disclosure, a system is provided. The system comprises an intraluminal imaging device, comprising: a flexible elongate member configured to be positioned within a body lumen of a patient, the flexible elongate member comprising a plurality of coaxial cables, wherein each of the plurality of coaxial cables comprises a conductive shield layer; and an ultrasound imaging assembly positioned at a distal portion of the flexible elongate member and in communication with the plurality of coaxial cables, the ultrasound imaging assembly comprising: a transducer array configured to obtain ultrasound data; and a conductive pad, wherein the conductive shield layer of each of the plurality of coaxial cables is mechanically and electrically coupled to the conductive pad; and a computer in communication with the intraluminal imaging device and configured to generate an ultrasound image based on the ultrasound data.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 8A is a top view of the interposer of FIG. 6A with a first row of coaxial cables connected according to an embodiment of the present disclosure.

DETAILED DESCRIPTION

Figure 1A:
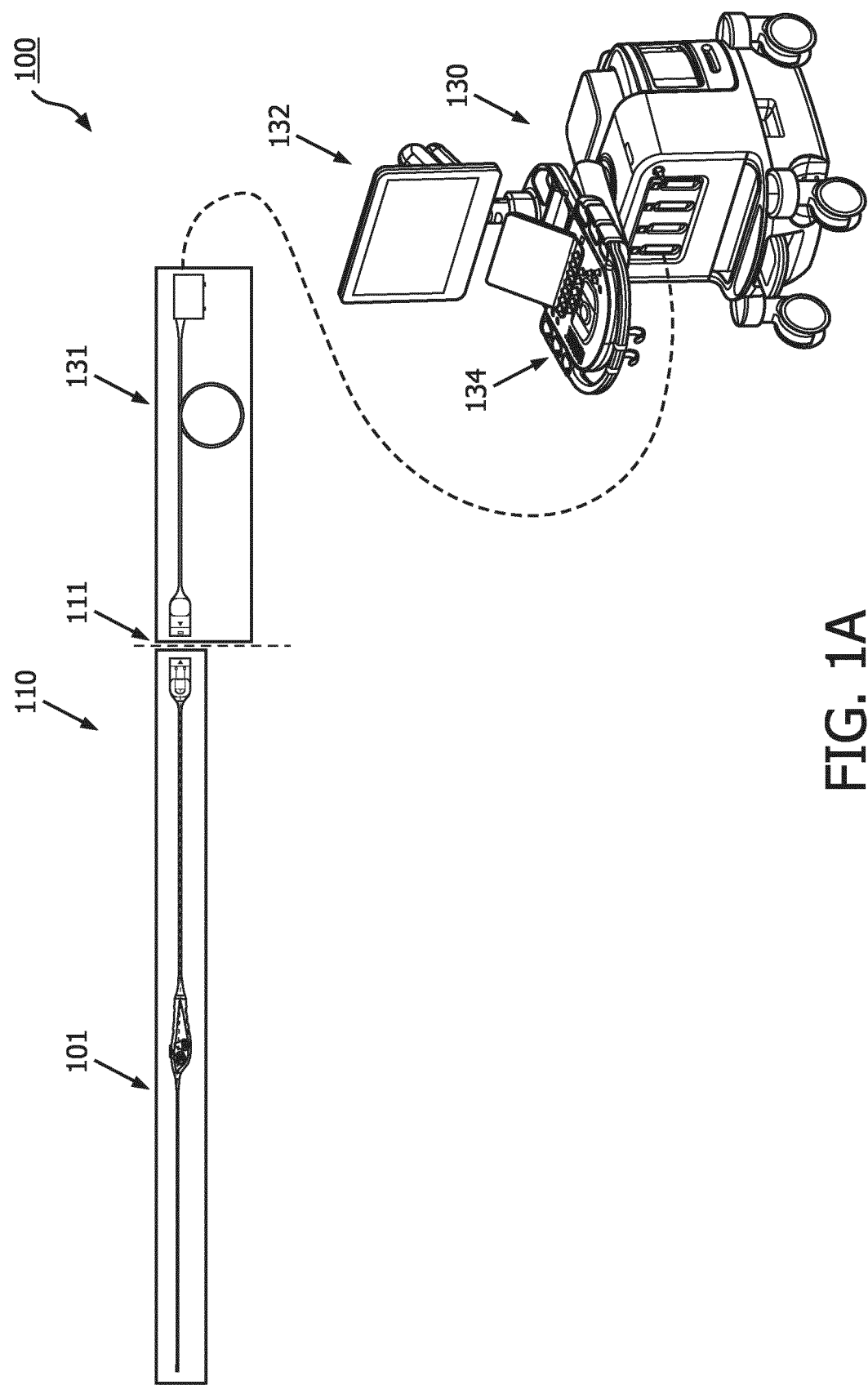
FIG. 1A is a schematic diagram of an intraluminal imaging system according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the present disclosure is described in terms of intraluminal imaging, it is understood that it is not intended to be limited to this application. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1A is a schematic diagram of an imaging system 100 according to embodiments of the present disclosure. The system 100 may include an intraluminal ultrasound imaging device 110, a control and processing system 130 (for example, a console including a computer), and a patient interface module (PIM) 131 extending between the device 110 and the control and processing system 130.

Figure 1B:
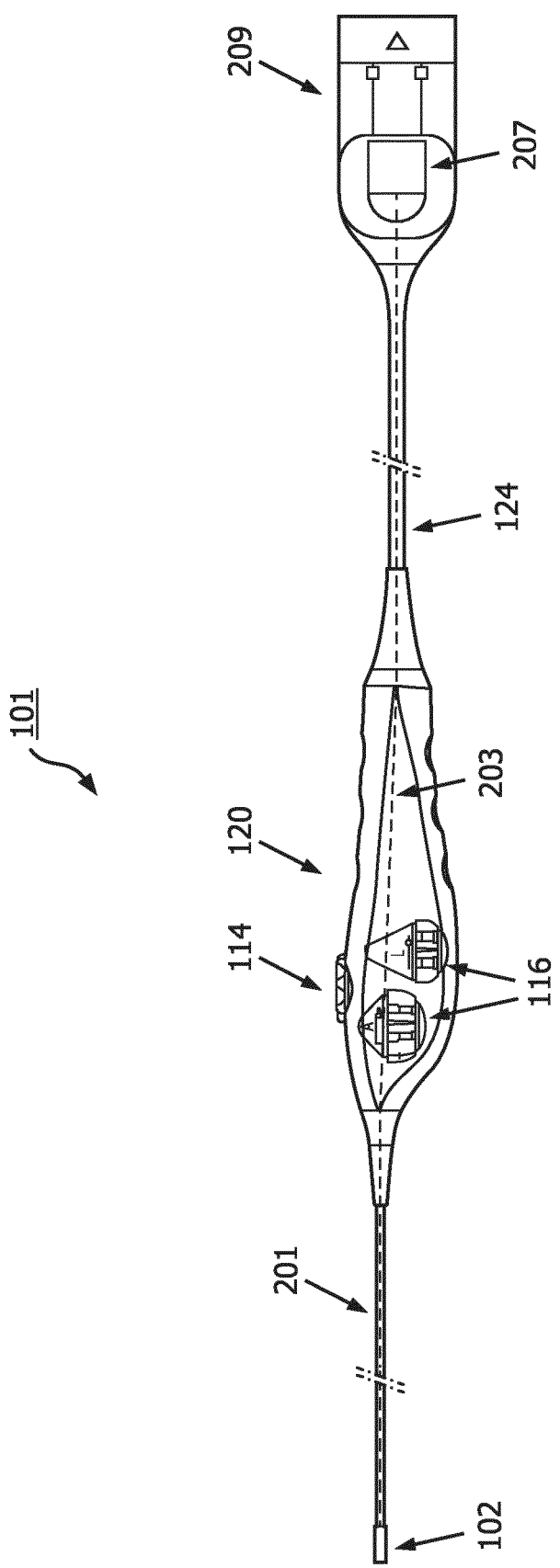
FIG. 1B is a schematic diagram of a catheter according to embodiments of the present disclosure.

The ultrasound imaging device 110 may include a catheter 101, which is shown in more detail in FIG. 1B. The catheter 101 may include one or more flexible elongate members sized and shaped, structurally arranged, and/or otherwise configured to be positioned within a body lumen of a patient. In some embodiments, the catheter 101 includes an ultrasound imaging assembly 102, a catheter body or shaft 201, a catheter cable 203, a handle 120, a conduit 124, a connector 209, and one or more printed circuit board assemblies (PCBAs) 207. The catheter cable 203 may have a small diameter configuration and a low profile that is sized to be passed or sneaked through a catheter shaft 201, the handle 120, and/or the conduit 124. The cable 203 may be electrically and/or mechanically coupled to the ultrasound imaging assembly 102 at the distal portion of the catheter shaft 201, as well as the PCBA 207 at the proximal portion of the catheter 101.

In some embodiments, one or both of the catheter body/shaft 201 and catheter cable 203 may be referred to as a flexible elongate member. The catheter shaft 201 is sized and shaped, structurally arranged and/or otherwise configured to be positioned within a body lumen of a patient (e.g., vasculature such as blood vessels or chambers of the heart). Respective portions of the catheter cable 203 extend within the catheter shaft 201, the handle 120, the conduit 124, and the connector 209. The imaging assembly 102 may be attached at a distal end of the catheter shaft 201. The catheter shaft 201 may include a lumen that the catheter cable 203 may pass through. The proximal end 204 shown in FIG. 2 of the catheter shaft 201 may be attached to the handle 120, for example, by a resilient strain reliever. The handle 120 may be used for manipulation of the ultrasound imaging device 110 and manual control of the ultrasound imaging device 110. The ultrasound imaging device 110 may include an imaging assembly 102 with ultrasound transducer elements and associated circuitry. The handle 120 may include actuators 116, a clutch 114, and other steering control components for steering the ultrasound imaging device 110. The steering may include deflecting the distal end of the catheter cable 203, as described in greater details herein.

The catheter cable 203 may pass through one or more of the catheter shaft 201, handle 120, conduit 124, and connector 209. In some embodiments, during assembly, the catheter cable 203 is sneaked through a lumen within the catheter body 201, handle 120, and conduit 124. In some embodiments, the conduit 124 is a component distinct from the cable 203. For example, the conduit can be a tubing within which the cable 203 extends. In other embodiments, the conduit 124 can be a coating defining an exterior surface of the cable 203. The coating can strengthen the cable 203 for exposure to direct contact and/or handling by an operator of the catheter 101. The catheter cable 203 may be terminated at a PCBA 207 within the connector 209. The catheter cable 203 may be electrically and mechanically coupled to the imaging assembly 102 and may include a plurality of electrical wires.

The handle 120 may be connected to the conduit 124 via another strain reliever. The conduit 124 may be configured to provide suitable configurations for interconnecting the control and processing system 130 and the monitor 132 to the imaging assembly 102. The control and processing system 130 may be used for processing, storing, analyzing, and manipulating data, and the monitor 132 may be used for displaying obtained signals generated by the imaging assembly 102. The control and processing system 130 can include a processor circuit with one or more processors in communication with memory. The memory can be a non-transitory computer readable storage medium. The memory can store instructions or program code that, when executed by the processor, causes the processing circuit to perform one or more functions described herein. The control and processing system 130 may be operable to facilitate the features of the intraluminal imaging system 100 described herein. For example, a processor can execute computer readable instructions stored on the non-transitory tangible computer readable medium. The control and processing system 130 can include one or more input devices, such as keyboards and any suitable command control interface device. The monitor 132 may be any suitable display device, such as liquid-crystal display (LCD) panel or the like.

In operation, a physician or a clinician may advance the catheter 101 into a lumen, such as a blood vessel, body lumen, or portion of a heart anatomy. By controlling actuators 116 and/or the clutch 114 on the handle 120, the physician or clinician may steer the catheter 101 to a position near the area of interest to be imaged. For example, one actuator may deflect the imaging assembly 102 and a distal end of the catheter cable 203 in a left-right plane and the other actuator may deflect the imaging assembly 102 and the distal end of the catheter cable 203 in an anterior-posterior plane. The clutch 114 may provide a locking mechanism to lock the positions of the actuators 116 and in effect lock the deflection of the imaging assembly 102 while imaging the area of interest.

The imaging process may include activating the ultrasound transducer elements on the imaging assembly 102 to produce ultrasonic energy. A portion of the ultrasonic energy is reflected by the area of interest and the surrounding anatomy, and the ultrasound echo signals are received by the ultrasound transducer elements. The conduit 124 may be used to transfer the received echo signals to the control and processing system 130 where the ultrasound image is reconstructed and displayed on the monitor 132. In some embodiments, the processing system 130 can control the activation of the ultrasound transducer elements and the reception of the echo signals. In some embodiments, the control and processing system 130 and the monitor 132 may be part of a same system.

While some embodiments of the present disclosure refer to an imaging device, an ultrasound imaging device, or an intraluminal imaging device, it is understood that the ultrasound imaging device 110 and the system 100 generally may be used to image vessels, structures, lumens, and/or any suitable anatomy/tissue within a body of a patient including any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the imaging device 110 may be used to examine man-made structures such as, but without limitation, heart valves, stents, shunts, filters and other devices. For example, the ultrasound imaging device 110 can be positioned within fluid filled or surrounded structures, both natural and man-made, such as within a body of a patient. The vessels, structures, lumens, and anatomy/tissue can include a blood vessel, such as an artery or a vein of a patient's vascular system, including cardiac vasculature, peripheral vasculature, neural vasculature, renal vasculature, and/or any suitable lumen inside the body.

The system 100 can be referenced as an imaging system, ultrasound imaging system, intraluminal imaging system, and/or combinations thereof. Although the present disclosure refers to ICE catheters, any suitable intraluminal imaging device is contemplated, such as an intravascular ultrasound (IVUS) device, an optical coherence tomography (OCT) device, an intracardiac echocardiography (ICE) device, a transesophageal echocardiography (TEE) device, an intravascular photoacoustic (IVPA) imaging device, and/or any suitable internal imaging device. Intraluminal devices with flexible elongate members such as catheters, guide wires, and/or guide catheter are contemplated.

The system 100 may be utilized in a variety of applications such as transseptal punctures, left atrial appendage closures, atrial fibrillation ablation, and valve repairs and can be used to image vessels and structures within a living body. Although the system 100 is described in the context of intraluminal imaging procedures, the system 100 is suitable for use with any catheterization procedure. In addition, the imaging assembly 102 may include any suitable physiological sensor or component for diagnostic, treatment, and/or therapy. For example, the imaging assembly can include an imaging component, an ablation component, a cutting component, a morcellation component, a pressure-sensing component, a flow-sensing component, a temperature-sensing component, and/or combinations thereof. In some embodiments, the intraluminal imaging system 100 is used for generating two-dimensional and three-dimensional images.

Referring back to FIG. 1A, the PIM 131 may provide a physical and electrical connection between the ultrasound imaging device 110 and the control and processing system 130. Some embodiments of the present disclosure omit the PIM 131. In other embodiments, the PIM 131 is communicatively interposed between the ultrasound imaging device 110 and the processing system 130. In some instances, the PIM 131 can be referenced as a patient interface cable. For example, a proximal connector 209 of the ultrasound imaging device 110, a distal connector of the PIM, and/or a proximal connector of the PIM may be configured to couple the ultrasound imaging device 110, the PIM 131, and the control and processing system together mechanically and electrically. The system 100 may include a connector junction 111 comprising a proximal connector 209 of the ultrasound imaging device 110 and the distal connector of the PIM 131.

In some embodiments, the control and processing system 130 may include one or more computers, processors, and/or computer systems. The control and processing system 130 may also be referred to as a console. In some embodiments, the PIM 131 is in mechanical and electrical communication with the control and processing system 130, such that the electrical signals are transmitted to the ultrasound imaging device 110 through the PIM 131 and to the control and processing system 130. The control and processing system 130 may include one or more processors and/or memory modules forming a processing circuit or processor circuit that may process the electrical signals, and generate and output a graphical representation of the imaging data on the monitor 132 (e.g., an ultrasound image). One or more electrical conductors of the ultrasound imaging device 110 and PIM 131 may facilitate communication between the control and processing system 130 and the ultrasound imaging device 110. For example, a user of the control and processing system 130 may control imaging using the ultrasound imaging device 110 via a control interface 134 of the control and processing system 130. Electrical signals representative of commands from the control and processing system 130 may be transmitted to the ultrasound imaging device 110 via connectors and/or cables in the PIM 131 and the ultrasound imaging device 110. The control and processing system 130 may be transportable and may include wheels or other devices to facilitate easy transportation by a user.

In some embodiments, the one or more components of the ultrasound imaging device 110 may be disposable components. For example, a user, such as a physician, may obtain the catheter 101 and/or the ultrasound imaging device 110 in a sterilized packaging. In some embodiments, the ultrasound imaging device 110 may be disposed after a single use. In other embodiments, the ultrasound imaging device 110 can be sterilized and/or re-processed for more than one use. The PIM 131 may be a re-usable component that is used in multiple procedures. For example, the PIM 131 can be cleaned between individual procedures, such as being treated with disinfectants to kill bacteria. In some embodiments, the PIM 131 may not be required to be sterilized before a medical procedure. For example, the PIM 131 can be sufficiently spaced from the patient such that use of a non-sterile PIM 131 is safe for the patient. The sterile-nonsterile connection at the connector assembly 111 between the ultrasound imaging device 110 and the PIM 131 may allow for a safe operating environment while saving costs by allowing expensive equipment to be reused.

Figure 2:
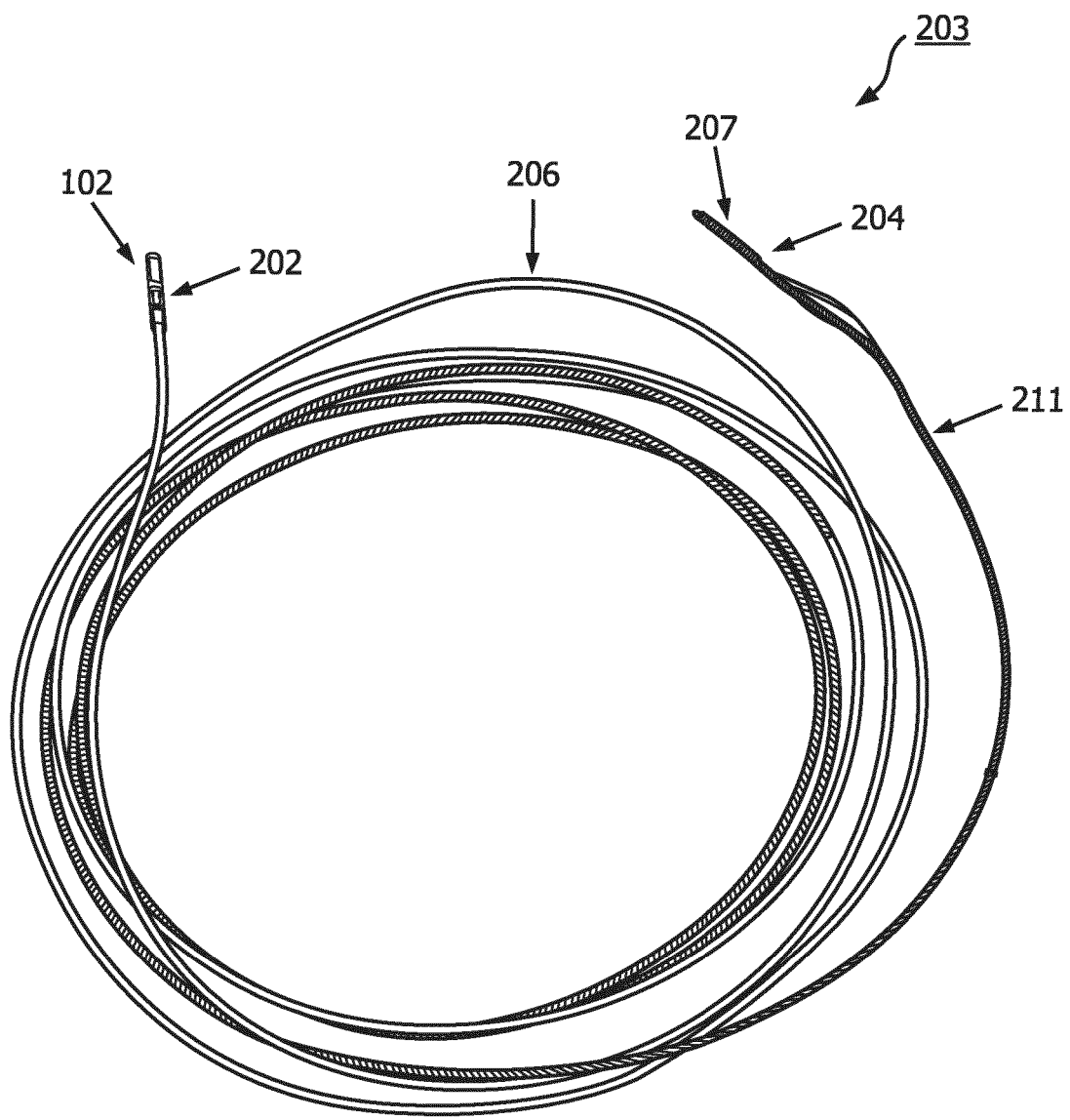
FIG. 2 is a perspective view of a catheter cable according to embodiments of the present disclosure.

FIG. 2 is a perspective view of the catheter cable 203 described above with respect to FIG. 1B. The catheter cable 203 is a flexible elongate body 206 including a plurality of communication cables allowing communication of imaging data and/or command signals between the processing system 130 and the catheter 101. The communication cables can be electrical wires. An individual electrical wire can include a bare single conductor surrounded by one or more insulating layer(s) and/or shielding layer(s). An individual electrical wire can also be a coaxial wire including a center conductor surrounded by one or more insulating layer(s) and a conductive shield layer also surrounded by one or more insulating or protective layer(s). The plurality of electrical wires collectively can be surrounded by one or more insulating layers(s) and/or shielding layer(s). An insulating layer may be formed of any suitable materials, such as a plastic or a polymer in some instances. A shield layer may be formed of any suitable material, such as a metal in some instances. For example, a woven layer 211, such as an RFI braid can surround the electrical wires. The cable 203 extends between the ultrasound imaging assembly 102 disposed at a distal portion 202 and PCBA 207 at a proximal portion 204. The flexible elongate body 206 extends between the distal end 202 and the proximal end 204. In some embodiments, the imaging assembly 102 is electrically and/or mechanically coupled (e.g., adhered or bonded) to distal end 202. During manufacturing, the imaging assembly 102 may be coupled to the catheter cable 203, prior to the cable 203 being sneaked through the catheter body or shaft. In some embodiments, the catheter cable 203 is about 4 feet long. In other embodiments, the catheter cable 203 is between 1 and 6 feet long or between 3 and 5 feet long, and/or other suitable values both larger and smaller.

Figure 3A:
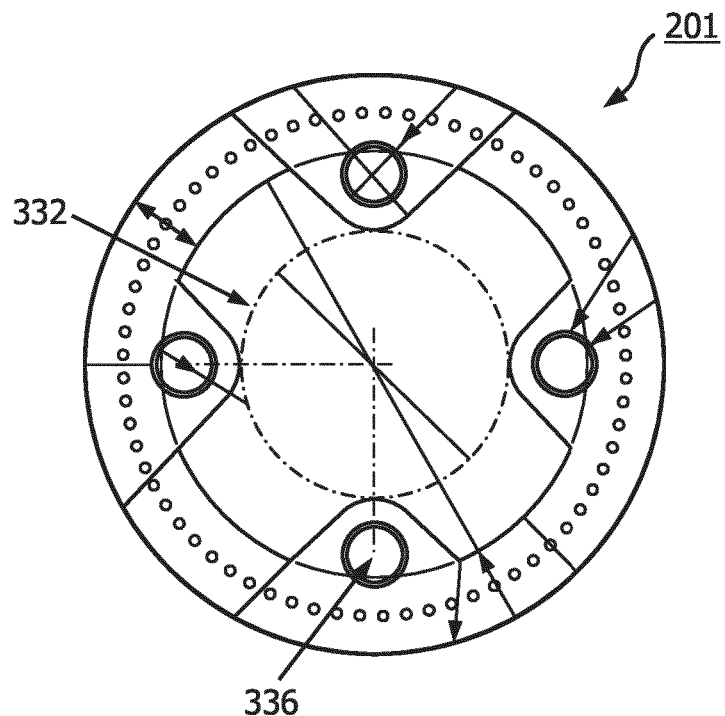
FIG. 3A is a cross-sectional view of a catheter body according to embodiments of the present disclosure.
Figure 3B:
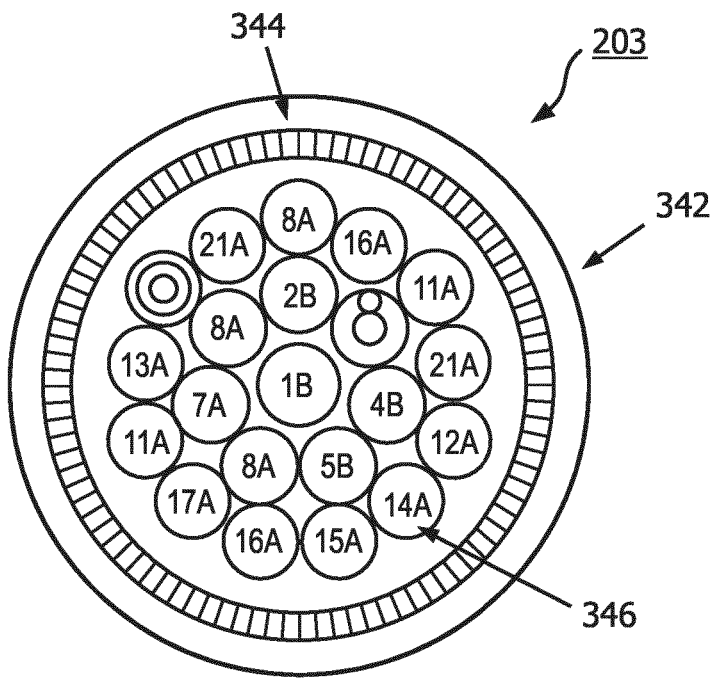
FIG. 3B is a cross-sectional view of a catheter cable according to embodiments of the present disclosure.

FIG. 3A shows a cross-sectional view of a catheter shaft 201. The catheter shaft 201 is sized and shaped, structurally arranged, and/or otherwise configured to be positioned within the body lumen of a patient during the imaging procedure. The catheter cable 203 (as shown in FIGS. 2 and 3B) may be configured to be disposed within an internal lumen 332 of the catheter shaft 201. The catheter shaft 201 may include a number of pullwire lumens 336 disposed within the catheter shaft 201. Pull wires positioned within the lumens 336 control movement (deflection of the distal tip) of the distal portion of the catheter shaft and/or the imaging assembly 102. In some embodiments, the catheter shaft 201 has an outer diameter between approximately 1 mm and approximately 3 mm, including values both larger and smaller. In an exemplary embodiment, the catheter shaft 201 has an outer diameter of about 1.422 (+/−0.025 mm).

FIG. 3B shows a cross-sectional view of a catheter cable 203. The catheter cable 203 (e.g., the PCBA 207 and the flexible elongate body 206) may be sneaked or passed through the catheter shaft 201 during assembly. The PCBA 207 can be configured to directly or indirectly interface with a user console. For example, the PCBA 207 can be in direct or indirect communication with the console or processing system 130 and/or the PIM 131 (FIG. 1A). In some embodiments, the catheter cable 203 has a diameter between approximately 1 mm and approximately 3 mm, including values both larger and smaller. In an exemplary embodiment, the catheter cable 203 has a diameter of about 1.3 mm (+/−0.07 mm). In some embodiments, the catheter cable 203 may include a polymer layer 342, a shielding layer 344, and a number of electrical wires 346. The electrical wires 346 may be disposed within the shielding layer 342 which may be disposed within the polymer layer 342. The electrical wires 346 may be used to communicate signals from the imaging assembly to the proximal end 204, and ultimately to the processing system 130. In some embodiments, the shield layer 342 can be the woven layer 211 disposed around the polymer layer 342, as shown in FIG. 2. The electrical wires 346 connect the imaging assembly 102 and the proximal connector 209 (e.g., PCBA 207).

Figure 4:
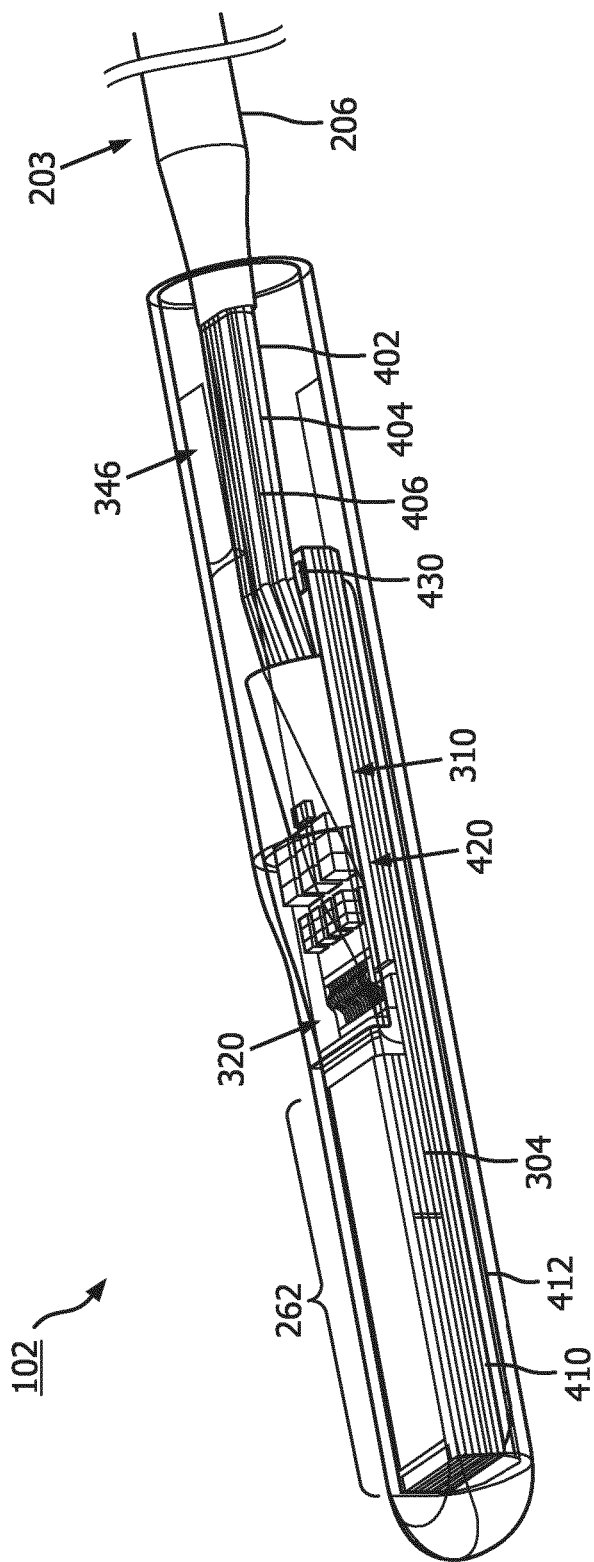
FIG. 4 is a perspective view of a distal ultrasound assembly of an intraluminal imaging device according to embodiments of the present disclosure.

FIG. 4 is a perspective view of the imaging assembly 102 according to embodiments of the present disclosure. The imaging assembly 102 is positioned at the distal portion of the catheter shaft 201 after assembly. The imaging assembly 102 is also positioned at the distal portion of the cable 203. The imaging assembly 102 may include an ultrasound transducer array 262 that includes a number of transducer elements and a micro-beam-former IC 304 that can be coupled to the transducer array 262. The electrical wires 346 of the cable 203 are mechanically and electrically coupled to the imaging assembly 102. In some examples, the electrical cable 203 is further coupled through an interposer 310 to the micro-beam-former IC 304. In some examples the interposer 310 is connected to the micro-beam-former IC 304 through wire bonding 320. The wires 346 of the cable 203 are directly or indirectly in communication with the transducer array 262, the IC 304, and/or the interposer 310. In some embodiments, the interposer 310 may be a circuit board or any other suitable component. In some embodiments, the wires 346 comprises three groups: a first set of coaxial cables 402, a second set of coaxial cables 404, and a third set of standard single conductor cables 406.

In some embodiments, the transducer array 262 includes ultrasound imaging transducers that are directly flip-chip mounted to the micro-beam-former IC 304. The transmitters and receivers of the ultrasound imaging transducers are on the micro-beam-former IC 304 and are directly attached to the transducers. In some examples, a mass termination of the acoustic elements is done at the micro-beam-former IC 304.

In some examples, the transducer array 262 includes more than 800 imaging elements and the electrical cable 203 includes a total of 12 signal lines or less. In some examples, the electrical cable 203 includes a total of 30 lines or less that includes the signal lines, power lines, and control lines. In some examples, the transducer array 262 includes a one-dimensional or two-dimensional array from between 32 to 1000 imaging elements. For example, the array can include 32, 64, 128, 256, 512, 640, 768, 812, or any other suitable number of imaging elements. For example, a one-dimensional array may have 32 imaging elements. A two-dimensional array may have 32, 64, or more imaging elements. In some examples, the number of signal lines is between 10 and 20, for example, 12 signal lines, 16 signal lines, or any other suitable number of signal lines. A one-dimensional array can be configured to generate two-dimensional images. A two-dimensional array can be configured to generate two-dimensional and/or three-dimensional images.

In some examples, the electrical cable 203 of the imaging assembly 102 is directly coupled to the micro-beam-former IC 304 of the imaging assembly 102. In some embodiments, the micro-beam-forming IC 304 lies directly underneath the transducer array 262 and is electrically connected to them. The elements of the transducer array 262 may be piezoelectric or micromachined ultrasonic transducer (MUT) elements. In some examples, piezoelectric elements are attached to the IC 304 by flip-chip mounting of an assembly of acoustic layers that include sawing into individual elements. MUT elements may be flip-chip mounted as a unit or grown directly on top of the micro-beam-former IC 304. In some examples, the cable bundle may be terminated to an interposer 310 of suitable material such as a rigid or flexible printed circuit assembly. The interposer 310 may then be connected to the micro-beam-forming IC 304 via any suitable means such as wire bondings 320.

In some embodiments, the micro-beam-forming IC 304 and the interposer 310 are coupled to an elongate acoustic backing material member 410. For example, adhesive bonding may be used. In other embodiments, micro-beam-former IC 304 and interposer 310 may be mechanically fastened, solvent bonded, UV bonded, ultrasonically welded, or coupled using any other suitable method. Acoustic backing 410 may extend from the distal tip of the micro-beam-former IC 304 to the proximal end of interposer 310.

A stiffening member 412 is coupled to acoustic backing 410. Stiffening member 412 may be of similar shape to acoustic backing 410 and also extend from the distal tip of the micro-beam-former IC 304 to the proximal end of the interposer 310. Stiffening member 412 provides additional rigidity and structure to imaging assembly 102. Stiffening member 412 may be composed of any suitable material. In an exemplary embodiment, stiffening member 412 is made of stainless steel. In other embodiments, stiffening member may be made of electroless nickel plating, titanium, carbon fiber, magnesium, high specific strength steel, other alloy steels, or other suitable materials.

Interposer 310 houses various electrical components 420. Electrical components 420 may be positioned between the distal termination of cables 326 and the wire bondings 320 and disposed on a top surface of interposer 310. In some embodiments, electrical components 420 may be used to generate, convey, amplify, attenuate, record, or smooth signals to and from the transducer array 262. Electrical components 420 may additionally by used for sensing one or more features of the physiology within which the intraluminal imaging device is positioned, such as the temperature. It is fully contemplated that electrical components 420 may serve any other function while positioned on imaging assembly 102. Electrical components may consist of both passive and active components, including but not limited to resistors, capacitors, inductors, transistors, operational amplifiers, thermistors, or any other suitable electrical component.

Interposer 310 may also include grounding pad 430. Grounding pad 430 may be a thin, conductive layer of material positioned on a top surface of interposer 310. Grounding pad 430 can be disposed at the proximal portion of interposer 310. A first set of coaxial cables 402 and a second set of coaxial cables 404 may be mechanically and electrically coupled to grounding pad 430. This connection may be achieved by soldering an exposed shield layer of each coaxial cable (e.g., exposed shield layer 710 of FIG. 7) in first set 402 and second set 404 such that the cables are mechanically and electrically bonded to grounding pad 430 as will be discussed in more detail herein. In some embodiments, coaxial cables may be preferred over single conductor cables because they transmit fast-switching, high frequency signals more effectively and reduce noise. In some embodiments, the coaxial cables can be configured to carry control signals from the computer 130 to the ultrasound imaging assembly 102 and/or image data from the ultrasound imaging assembly 102 to the computer 130.

Figure 5:
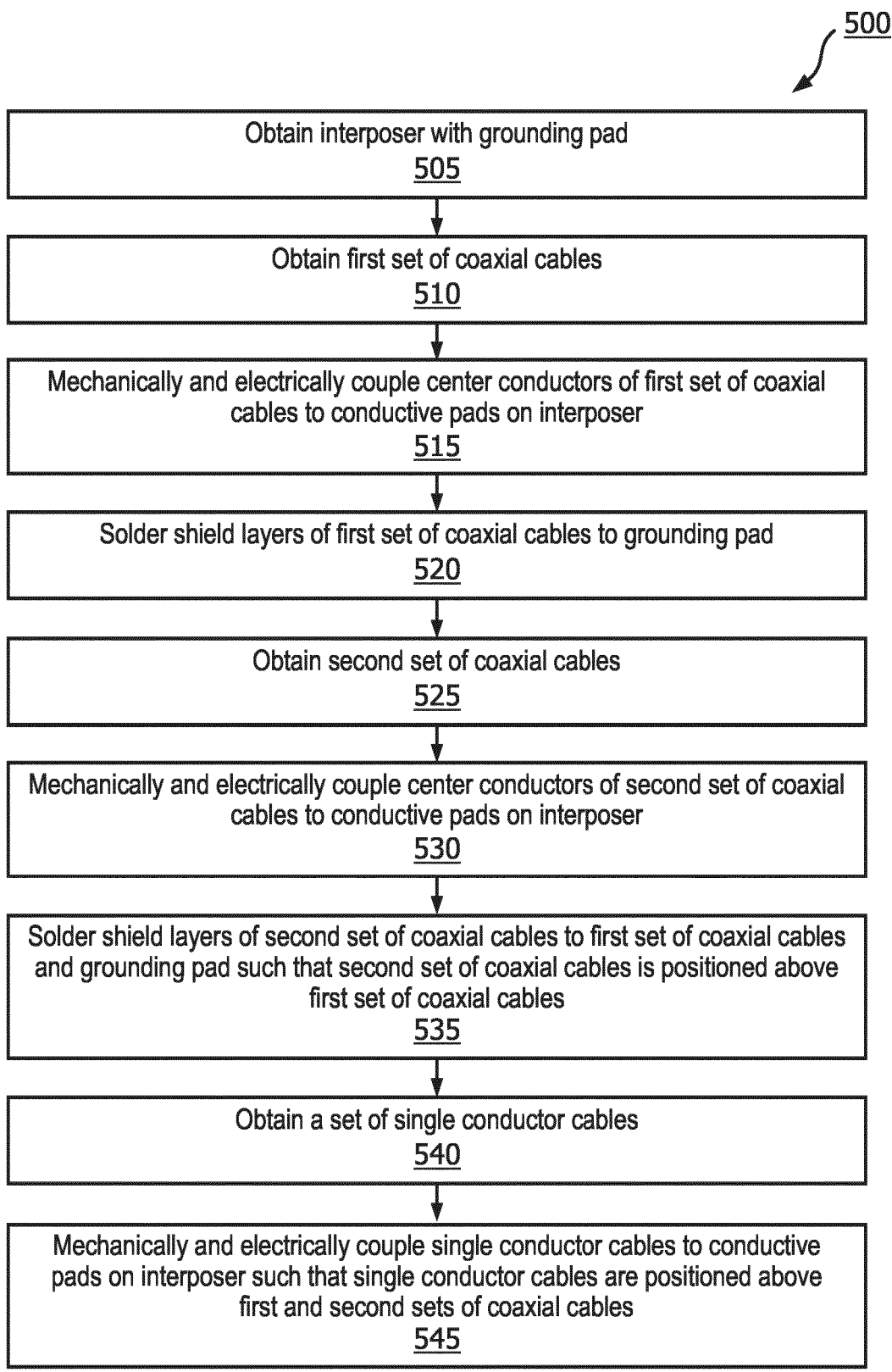
FIG. 5 is a flow chart diagram of a method of assembling an intraluminal imaging device according to an embodiment of the present disclosure.

FIG. 5 is a flow chart diagram of a method 500 of assembling an intraluminal imaging device 101 according to an embodiment of the present disclosure. The method 500 can include connecting the ultrasound imaging assembly 102 to the catheter cables 346. As illustrated, method 500 includes a number of enumerated steps, but embodiments of method 500 may include additional steps before, after, or in between the enumerated steps. In some embodiments, one or more of the enumerated steps may be omitted, performed in a different order, or performed concurrently. The steps of method 500 can be carried out by a manufacturer of the intraluminal imaging device 101, a manufacturer of a subassembly including the ultrasound imaging assembly 102 or the catheter cables 346, and/or a manufacturer of any other component discussed in the present disclosure. Method 500 will be described with reference to FIGS. 6A-11, which are diagrammatic views of various components of the ultrasound imaging assembly 102 and cables 346 during various steps of manufacturing. For example, FIGS. 6A-11 illustrate assembly steps for various components of the device 110, such as the connection between the ultrasound imaging assembly 102 and cables 346.

Figure 6A:
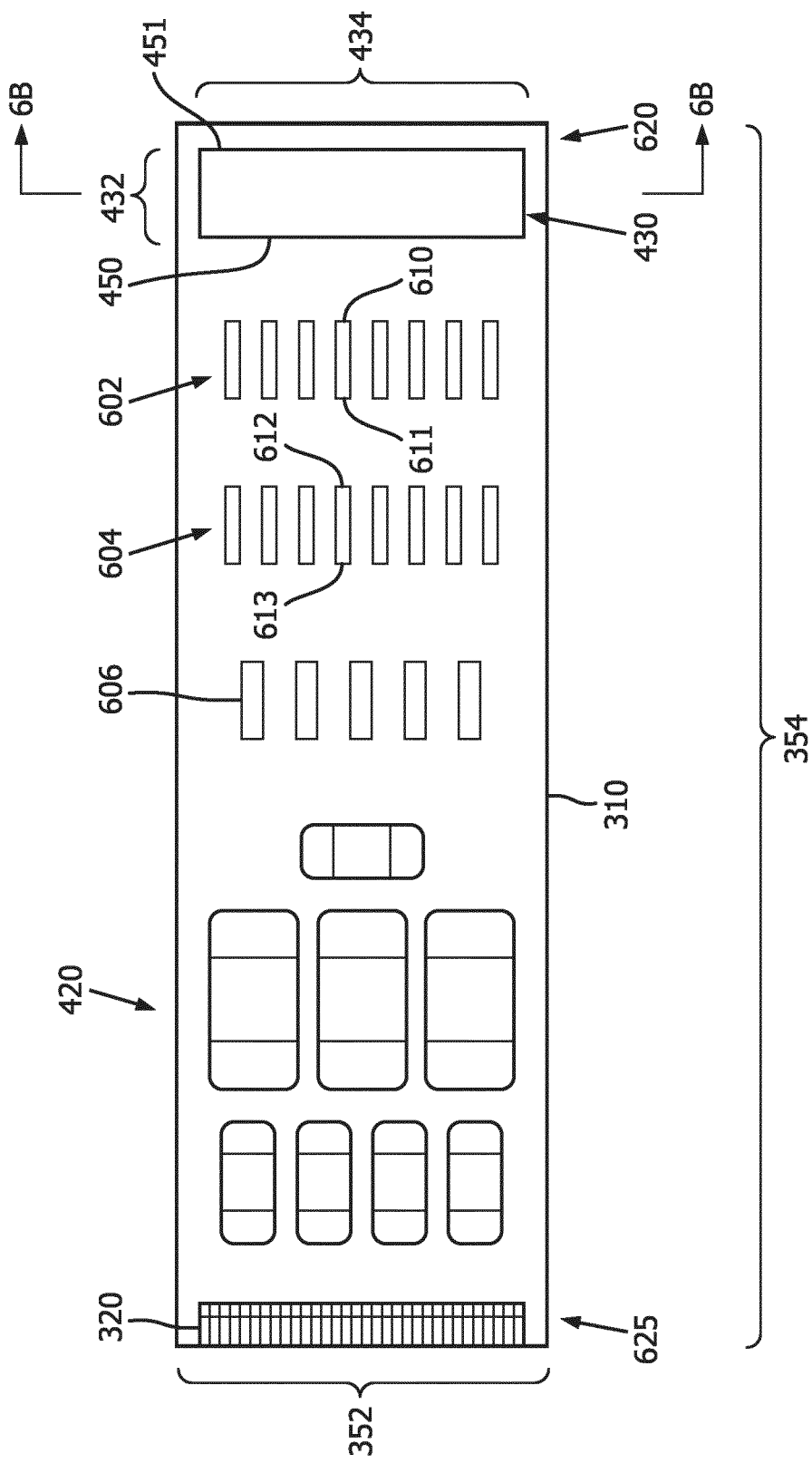
FIG. 6A is a top view of an interposer before catheter cables are connected according to an embodiment of the present disclosure.

At step 505, method 500 includes obtaining an interposer 310 with a grounding pad 430 disposed on a surface thereof, such as a top or superior surface. A diagrammatic top view of an exemplary interposer 310 with grounding pad 430 positioned at a proximal portion 620 of interposer 310. is illustrated in FIG. 6A, according to an embodiment of the present disclosure. Various components of the ultrasound imaging assembly 102 can be coupled to the interposer 310. In some embodiments, interposer 310 may be a circuit board facilitating electrical communication between one or more components of the device 101, such as the cables 346, transducer array 262, and/or the IC 304. The circuit board can include conductive traces formed on a surface and/or an interior thereof. The interposer board can be formed of any suitable semiconductor material, such as a silicon (Si) substrate or a germanium (Ge) substrate. In some embodiments, interposer 310 may include a compound semiconductor such as silicon carbide (SiC), silicon germanium (SiGe), silicon germanium carbide (SiGeC). As shown in FIG. 6A, conductive pads 602, 604, and 606 may be disposed on a top surface of interposer 310. Electrical components 420 may also be disposed on a top surface of interposer 310. Electrical components 420 may be of any particular type as discussed previously. Conductive pads 602, 604, and 606 may be positioned along a length of the interposer 310 between grounding pad 430 and electrical components 420. Conductive pads 602 may have a proximal end 610 and a distal end 611. Conductive pads 604 may also have a proximal end 612 and a distal end 613. Additionally, grounding pad 430 may have a proximal end 451 and a distal end 450. Electrical components 420 may positioned at a location distally from conductive pads 602, 604, or 606. Wire bondings 320 may also be positioned on a top surface of interposer 310 and disposed at the distal portion 625 of the interposer 310. The arrangement of the conductive pads 602, 604, and 606, electrical components 420, and/or the wire bondings 320 in the illustrated embodiment of FIG. 6A is merely illustrative. Any of these features may also be positioned at any location on interposer 310.

The interposer 310 can include dimensions 352, 354, and 356 which may be of any suitable size. The dimension 352 can be a width, the dimension 354 can be a length, and the dimension 356 can be a depth. In some embodiments, the width 352 of interposer 310 may be between approximately 1 mm and approximately 3 mm, including values both larger and smaller. In an exemplary embodiment, the width 352 of interposer 310 is about 2.31 mm (+/−0.100 mm). In some embodiments, the length 354 of interposer 310 may be between approximately 8 mm and approximately 15 mm, including values both larger and smaller. In an exemplary embodiment, the length 354 of interposer 310 is about 11.5 mm (+/−0.100 mm). The depth 356 of interposer 310 may be between approximately 0.10 mm and approximately 0.40 mm, including values both larger and smaller. In an exemplary embodiment, the depth 356 of interposer 310 is about 0.25 mm (+/−0.100).

The grounding pad 430 can include dimensions 432, 434, and 436, which may be of any suitable size. The dimension 434 can be a width, the dimension 432 can be a length, and the dimension 436 can be a depth. Generally, the width 434 of grounding pad 430 is similar to or less than the width 352 of interposer 310. Width 434 may be the same as width 352. Length 432 of grounding pad 430 may generally be the same as length 712 of the exposed shield layer 710 of coaxial cables 700 shown in FIG. 7 and as will be discussed in more detail herein. The length 432 of grounding pad 430 may be of any suitable length as to allow room for other components on interposer 310 and create a necessary bonding between cables 346 and interposer 310. In some embodiments, the length 432 of grounding pad 430 may be between approximately 0.5 mm and approximately 1.0 mm, including values both larger and smaller. In an exemplary embodiment, the length 432 of grounding pad 430 is about 0.69 mm (+/− 0.050 mm). In some embodiments, the width 434 of grounding pad 430 may be between approximately 1.0 mm and approximately 3.0 mm, including values both larger and smaller. In an exemplary embodiment, the width 434 of grounding pad 430 is about 1.85 mm (+/−0.050 mm).

Figure 6B:
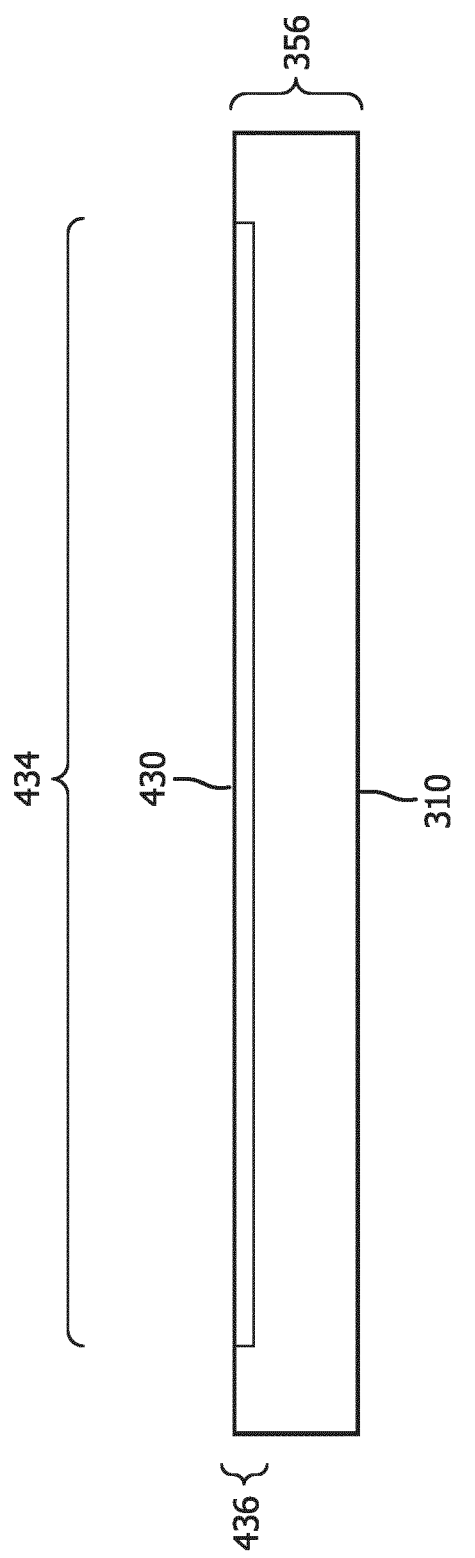
FIG. 6B is a cross-sectional view of the interposer along section line 6B-6B in FIG. 6A before catheter cables are connected according to an embodiment of the present disclosure.

Referring now to FIG. 6B, shown therein is a diagrammatic cross-sectional view of interposer 310 and grounding pad 430 along section line 6B-6B in FIG. 6A. As depicted in FIG. 6B, grounding pad 430 is a generally rectangular, thin conductive material disposed on interposer 310. In some embodiments, the depth 436 of grounding pad 430 may be between approximately 0.010 mm and approximately 0.100 mm, including values both larger and smaller. In an exemplary embodiment, the depth 436 of grounding pad 430 is about 0.025 mm (+/−0.005 mm). In FIG. 6B, grounding pad 430 is depicted as being recessed into a corresponding cavity on a top surface of interposer 310 so as to make the top surface of grounding pad 430 level, flush, or continuous with the top surface of interposer 310. This configuration represents one illustrative embodiment. It will be understood that grounding pad 430 may be disposed on top of interposer 310 without a recessed cavity such that grounding pad 430 protrudes from the upper surface of interposer 310 by a distance generally equal to depth 436 of grounding pad 430. Alternatively, grounding pad 430 may be recessed into interposer 310 by a depth greater than depth 436 such that the upper surface of grounding pad 430 lies beneath the upper surface of interposer 310. The exact orientation of grounding pad 430 in relation to interposer 310 may be of any particular type.

Figure 7:
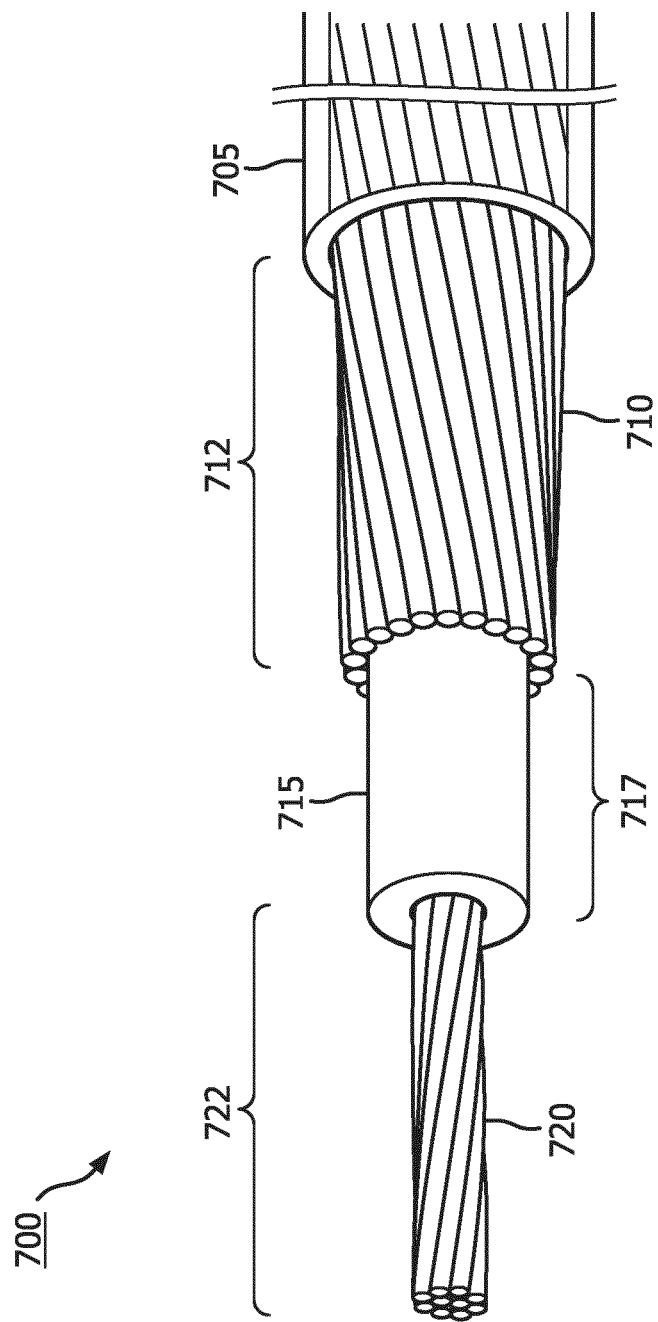
FIG. 7 is a perspective view of a coaxial cable with each layer partially exposed according to an embodiment of the present disclosure.

Referring again to FIG. 5, at step 510, method 500 includes obtaining a first set of coaxial cables. An illustrative example of one embodiment of a coaxial cable that may be included in this first set of coaxial cables is shown in FIG. 7. Coaxial cable 700 includes four basic layers. It is fully contemplated that additional layers may be added to those shown in FIG. 7. For example, layers that provide additional strength, rigidity, protection, increased conductivity, or any other function may be added to coaxial cable 700. For example, an inner shielding layer and an outer shield layer can be provided. The inner shield layer and/or the outer shield layer can be electrically and mechanically coupled to other components within ultrasound imaging assembly 102. For simplicity's sake, only four layers are shown and discussed in detail herein.

A center conductor cable 720 may be positioned along the axial center of cable 700. The center conductor 720 may comprise multiple conductive elongate wires twisted or otherwise coupled to one another or may comprise a single conductive elongate wire. The center conductor 720 may carry a signal from the control and processing system 130 to the ultrasound image assembly 102 or from the ultrasound imaging assembly 102 to the control and processing system 130. Coaxial cable 700 may be provided in such a way that layers of cable 700 are removed to expose a distal portion of center conductor 720 of a length 722. Cable 700 may be obtained with this distal portion of center conductor 720 already exposed. The length 722 of the distal portion of center conductor 720 may be of any suitable length. Length 722 will generally be of similar dimensions to conductive pads 602 or 604 so as to make electrical and mechanical bonding of the distal end of center conductor 720 to conductive pad 602 or 604 possible as will be discussed in more detail herein.

An insulation layer 715 may be disposed around center conductor 720. The insulation layer 715 may extend primarily from the proximal to distal ends of center conductor 720. A purpose of insulation layer 715 may be to insulate center conductor 720 from other layers of cable 700 and from the surrounding environment such that center conductor 720 is not in electrical communication with any elements except those intended at either end of center conductor 720. As previously mentioned, insulation layer 715 is not disposed around a distal portion of center conductor 720 to allow electrical and mechanical bonding of the distal end of center conductor 720 to a conductive pad 602 or 604. As shown in FIG. 7, outer layers of cable 700 are further removed to expose a length 717 of insulation layer 715. Length 717 may be of any suitable length. Generally, length 717 may be approximately equal to the distance from the proximal end 610 of conductive pads 602 to the distal end 450 of grounding pad 430 for first set of coaxial cables 700a. For a second set of cables 700b, length 717 is approximately equal to the distance from the proximal end 612 of conductive pads 604 to the distal end 450 of grounding pad 430, further accounting for any displacement of coaxial cables 700b as a result of being positioned over cables 700a as will be discussed herein.

A shield layer 710 may be positioned around insulation layer 715 extending primarily from the proximal to distal ends of insulation layer 715. A purpose of shield layer 710 may be to establish an electrical ground relative to center conductor 720 in electrical communication with control and processing system 130 and ultrasound imaging assembly 102. Like the exposed distal portion of center conductor 720, and the exposed distal portion of insulation layer 715, an outer layer or jacket 705 of coaxial cable 700 is partially removed to expose a distal portion of shield layer 710. As mentioned previously, the length 712 of this exposed distal portion of shield layer 710 is generally of the same or similar length as the width 432 of grounding pad 430. However, the length 712 of the exposed distal portion of shield layer 710 may be of any suitable length.

An outer layer or jacket 705 is disposed around the shield layer 710 extending primarily from the proximal to distal ends of shield layer 710. A purpose of jacket 705 may be to insulate shield layer 710 from the general environment and ensure that shield layer 710 is only in electrical communication with the control and processing system 130 and the ultrasound imaging assembly 102. As previously stated, jacket 705 is removed to expose a distal portion of shield layer 710 of a length 712 as shown in FIG. 7.

Referring again to FIG. 5, at step 515, method 500 includes mechanically and electrically coupling center conductors 720a of a first set of coaxial cables 700a to conductive pads 602 on interposer 310. As shown in FIG. 8A, a first set of coaxial cables 700a are substantially similar to one another. FIG. 8A depicts eight such coaxial cables positioned on interposer 310, however, it is fully contemplated that any number of coaxial cables 700a may be included in this first set. A first set of coaxial cables 700a may include only one coaxial cable 700a, two, four, eight, sixteen, or more of coaxial cables 700a.

As shown in FIG. 8A, the center conductor 720a of each coaxial cable 700a is mechanically and electrically bonded to a corresponding conductive pad 602 positioned on interposer 310. Because eight coaxial cables 700a are shown in FIG. 8A, interposer 310 has eight conductive pads 602 positioned on interposer 310 near grounding pad 430. As mentioned, this number is merely illustrative. An electrical and mechanical bond may be achieved by any suitable method, including but not limited to using solder.

Figure 8B:
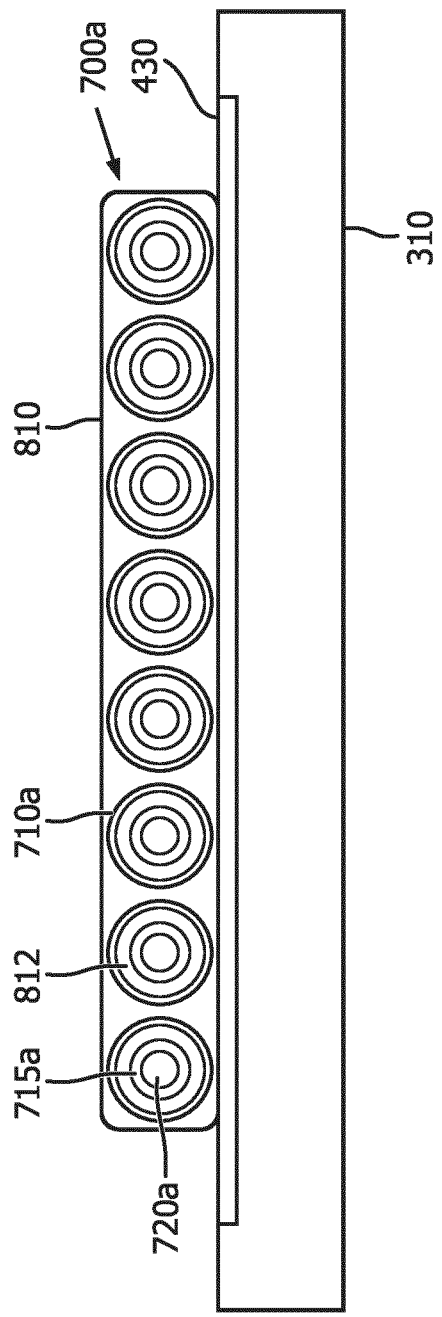
FIG. 8B is a cross sectional view of the interposer along section line 8B-8B in FIG. 8A with a first row of coaxial cables connected according to an embodiment of the present disclosure.

Referring again to FIG. 5, at step 520, method 500 includes soldering shield layers 710a of coaxial cables 700a to grounding pad 430. In some embodiments a mass of solder 810 as shown in FIG. 8B is applied such that shield layers 710a of coaxial cables 700a are mechanically and electrically bonded to grounding pad 430. As each shield layer 710a of coaxial cables 700a is to carry an equivalent electrical ground respective to the signal carried by each center conductor 720a of coaxial cables 700a, each shield layer 710a of coaxial cables 700a may be in electrical communication with each other and with grounding pad 430. Grounding pad 430 provides an electrical ground for the plurality of coaxial cables 700a and the plurality of coaxial cables 700b as described in more detail herein. In addition to establishing an electrical connection, between shield layers 710a, solder mass 810 provides a mechanical connection between coaxial cables 700a and interposer 310 such that the connection between catheter cables 346 and ultrasound image assembly 102 is significantly stronger than traditional methods.

FIG. 8B is a cross-sectional view of interposer 310 along section line 8B-8B in FIG. 8A, with first row of coaxial cables 700a connected according to an embodiment of the present disclosure. Eight coaxial cables 700a are shown disposed over the upper surface of grounding pad 430 as previously mentioned. At the axial center of each coaxial cable is shown center conductor 720a. Positioned around each center conductor 720a is insulation layer 715a. Positioned around each insulation layer 715a is shown shield layer 710a. Between insulation layer 715a and shield layer 710a is shown a layer of solder 812 that passes through shield layer 710a during the soldering process. Solder 812 may be a part of or substantially similar to solder mass 810. Shield layer 710a may be constructed out of a braided conductive material so as to allow solder to pass through the layer. Alternatively, shield layer 710a may be constructed of any suitable conductive material that allows solder to pass through the layer. In still other embodiments, shield layer 710a may not be porous at all and not allow solder to pass through the layer but still provides a strong mechanical connection. Shield layer 710a is at least semi-porous to allow solder to pass through the layer as the resulting intertwined connection ensures a stronger mechanical connection between solder mass 810 and shield layer 710a and subsequently between first set of coaxial cables 700a and interposer 310.

Without the solder mass as described in the present application, the connection between the distal tip of the ICE catheter, with ultrasound imaging assembly, and more proximal portions of the ICE catheter, such as the catheter shaft, are relatively weaker. For example, the distal tip and the catheter shaft are attached at a polymer-polymer interface between a polymer housing of the distal tip and the polymer forming the catheter shaft. The center conductors of the cables are also attached to their respective conductive pads for electrical communication. However, these connections are weaker and cannot handle larger tensile forces (e.g., at least 15 N). Advantageously, mechanically coupling the shield layers of the plurality of coaxial cables to the grounding pad 430 via the solder mass as described in the present disclosure provides a strong mechanical connection between electrical wires 346 and ultrasound imaging assembly 102. The solder mass connection thus provides a stronger point of connection between the distal tip of the ICE catheter and more proximal portions (e.g., stronger than the polymer-polymer interface and the center conductor-conductive pad connection). The presently disclosed method and apparatus advantageously satisfy minimum peak tensile force requirements in ISO 10555, among other national and international requirements of peak tensile force for intra-cardiac echocardiography (ICE) catheters that have a catheter shaft diameter larger than 1.85 mm. In some embodiments, the catheter shaft 201 (FIG. 3A) has a diameter of 9 Fr (3 mm). For example, the solder mass 810 is configured to support a tensile load of at least 15 N. For example, the solder mass 810 is configured to support a tensile load between approximately 1 N and approximately 60 N, between approximately 15 N and approximately 60 N, and/or other values both larger and smaller.

Solder mass 810 takes the same general shape of grounding pad 430 as the solder will wick to all conductive surfaces it comes in contact with and avoid mechanical bonding with non-conductive surfaces. For example, the solder mass can have a generally shaped as a rectangular or polygonal prism, with a generally rectangular or polygonal cross-sectional profile. In some embodiments, interposer 310 is constructed of a non-conductive material such that solder mass 810 only bonds with grounding pad 430 and shield layers 710a. In addition, insulation layer 715a and jacket 705a of coaxial cables 700a are constructed of non-conductive material such that solder mass 810 does not electrically or mechanically bond with these elements as well resulting in solder mass 810 retaining a shape generally similar to grounding pad 430.

Referring again to FIG. 5, at step 525, method 500 includes obtaining a second set of coaxial cables 700b. The second set of coaxial cables 700b may be substantially similar to first set of coaxial cables 700a. An illustrative example of one embodiment of a coaxial cable 700 in this second set 700b is shown in FIG. 7.

Second set of coaxial cables 700b may differ from the first set of coaxial cables 700a in regards to length 717 of insulation layer 715. Referring again to FIG. 6A, length 717 of insulation layer 715 of coaxial cables 700b may be the same general length as the distance between the proximal end 604b of conductive pads 604 and the distal end 430a of grounding pad 430. The length 717 of insulation layer 715 of coaxial cables 700b may be slightly longer than this distance due to an offset of the location of cables 700b as cables 700b may be positioned above first set of coaxial cables 700a.

Figure 9A:
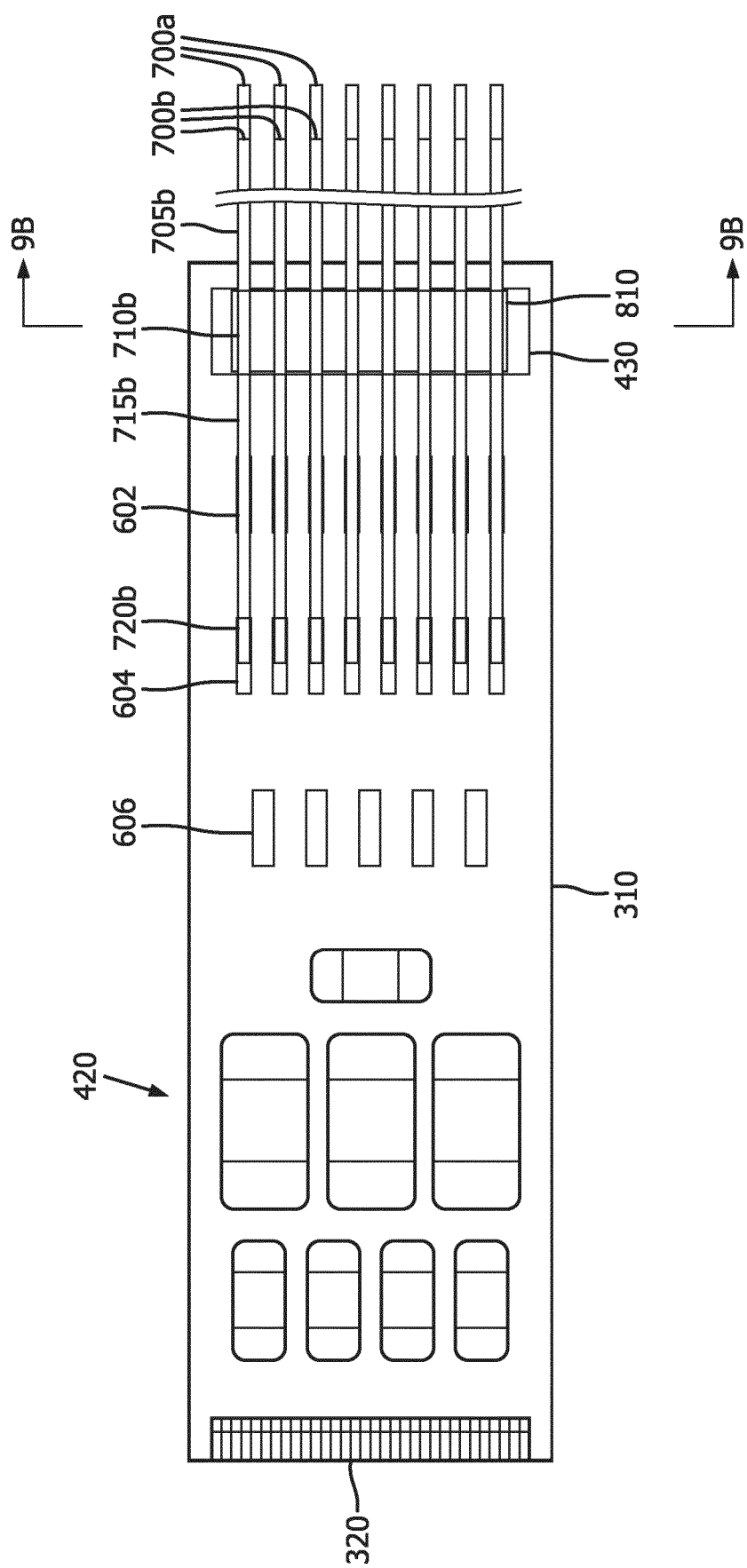
FIG. 9A is a top view of the interposer of FIG. 6A with first and second rows of coaxial cables connected according to an embodiment of the present disclosure.

Referring again to FIG. 5, at step 530, method 500 includes mechanically and electrically coupling center conductors 720b of a second set of coaxial cables 700b to conductive pads 604 on interposer 310. As shown in FIG. 9A, a second set of coaxial cables 700b are positioned over the top of a first set of coaxial cables 700a. Like cables 700a, coaxial cables 700b are each substantially similar to one another. FIG. 9A depicts eight such coaxial cables 700b positioned on interposer 310 and eight coaxial cables 700a positioned beneath coaxial cables 700b. FIG. 9A therefore shows 16 coaxial cables 700 positioned on interposer 310, however, it is fully contemplated that any number of coaxial cables 700 may be included. Similarly, a second set of coaxial cables 700b may include only one coaxial cable 700b, two, four, eight, sixteen, or more of coaxial cables 700b.

Figure 9B:
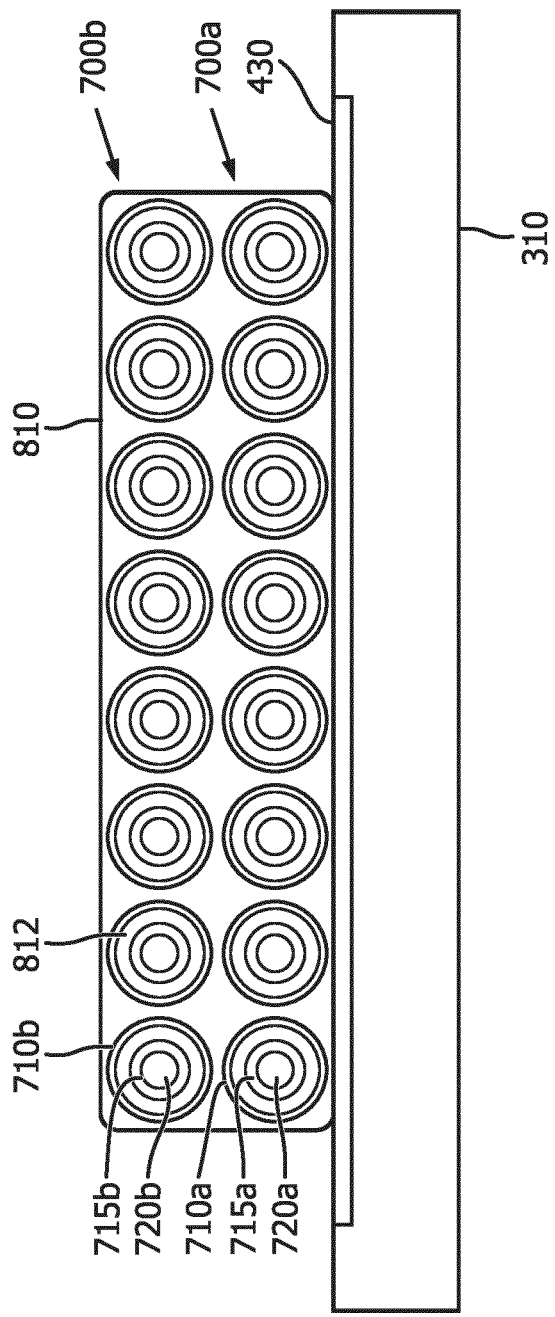
FIG. 9B is a cross-sectional view of the interposer along section line 9B-9B in FIG. 9A with first and second rows of coaxial cables connected according to an embodiment of the present disclosure.

As shown in FIG. 9A, center conductor 720b of each coaxial cable 700b is mechanically and electrically bonded to a corresponding conductive pad 604 positioned on interposer 310. Because eight coaxial cables 700b are shown in FIG. 9A, interposer 310 shows eight conductive pads 604. As mentioned, this number is merely illustrative. In some embodiments, conductive pads 602 may be positioned between conductive pads 604 and grounding pad 430. This orientation allows the second set of coaxial cables 700b to be positioned over the first set of coaxial cables 700a so as to create two rows of coaxial cables as shown in FIG. 9B. Arranging coaxial cables 700a and 700b over one another in two rows with conductive pads 602 and 604 arranged in two corresponding rows allows all cables 346 to be terminated and mechanically and electrically coupled to interposer 310 in less space on interposer 310 than traditional methods. This configuration of two or more rows of coaxial cables as disclosed in the present invention makes the entire ultrasound imaging assembly 102 shorter which allows for easier maneuvering of the intraluminal catheter assembly 101 within the heart, vasculature, or other lumen within a patient. A mechanical and electrical bond between center conductors 720b and conductive pads 604 may be achieved by any suitable method, including but not limited to using solder.

Referring again to FIG. 9A, the proximal portions of first set of coaxial cables 700a and second set of coaxial cables 700b are depicted as being offset from one another, such that second set of coaxial cables 700b appear to terminate at some location distal of the proximal termination of first set of coaxial cables 700a. Although this orientation may be utilized in an embodiment of the present disclosure, this staggering of the proximal termination of coaxial cables is depicted for primarily pedagogical purposes to show that first set of coaxial cables 700a are positioned beneath second set of coaxial cables 700b despite second set of coaxial cables 700b completely obscuring the view of first set of coaxial cables 700a in FIG. 9A.

Referring again to FIG. 5, at step 535, method 500 includes soldering shield layers 710b of coaxial cables 700b to grounding pad 430. In some embodiments, the mass of solder 810 which was applied to shield layers 710a of first set of coaxial cables 700a is expanded to further encompass shield layers 710b of second set of coaxial cables 700b and shield layers 710a of first set of coaxial cables 700a. In this manner, shield layers 710b of second set of coaxial cables 700b are mechanically and electrically bonded to both shield layers 710a of first set of coaxial cables 700a and grounding pad 430. As each shield layer 710a and 710b of coaxial cables 700a and 700b carry an equivalent electrical ground respective to the signal carried by each center conductor 720a and 720b of coaxial cables 700a and 700b, each shield layer 710a and 710b of coaxial cables 700a and 700b may be in electrical communication with each other and with grounding pad 430. In addition to establishing an electrical connection between shield layers 710a, 710b, and grounding pad 430, solder mass 810 provides a mechanical connection between coaxial cables 700a, 700b, and interposer 310 such that the connection between catheter cables 346 and ultrasound image assembly 102 is significantly stronger than traditional methods.

FIG. 9B is a cross-sectional view of interposer 310 along section line 9B-9B in FIG. 9A, with a first row of coaxial cables 700a and a second row of coaxial cables 700b bonded to grounding pad 430 according to an embodiment of the present disclosure. Eight coaxial cables 700a are shown disposed along the upper surface of grounding pad 430 as previously mentioned. Further, eight coaxial cables 700b are shown disposed along the upper surfaces of the first set of coaxial cables 700a. Similar to first set of coaxial cables 700a, second set of coaxial cables 700b may include a shield layer 710b that is at least semi-porous so as to allow a small amount of solder 812 to pass through shield layer 710b and ensure a stronger mechanical connection between solder mass 810 and shield layer 710b and subsequently between second set of coaxial cables 700b, first set of coaxial cables 700a, and interposer 310.

Solder mass 810 still retains the same general shape of grounding pad 430 as the solder will wick to all conductive surfaces it comes in contact with and avoid mechanical bonding with non-conductive surfaces. In some embodiments, interposer 310 is constructed of a material such that solder mass 810 only bonds with grounding pad 430 and shield layers 710a and 710b. In addition, insulation layer 715b and jacket 705b of coaxial cables 700b are constructed of non-conductive material such that solder mass 810 does not electrically or mechanically bond with these elements as well. Solder mass 810 has a width similar to width 434 of grounding pad 430 and a length similar to length 432 of grounding pad 430. The vertical depth of solder mass 810 is largely dependent on the dimensions and positions of coaxial cables 700a and 700b. The vertical depth of solder mass 810 may be between approximately 0.25 mm and approximately 0.75 mm, including values both larger and smaller. In an exemplary embodiment, the vertical depth of solder mass 810 is about 0.50 mm (+1-0.10 mm). The solder mass completely or partially surrounds a perimeter of each of the coaxial cables. For example, in a cross-section of the coaxial cables, the solder mass can completely or partially surround one or more of the coaxial cables. The solder mass 810 extends within lateral and vertical space between adjacent coaxial cables. For example, solder mass 810 will fill space between coaxial cables positioned left and right of each other within the same set and will fill space between coaxial cables positioned above and below each other within first set of coaxial cables 700a and second set of coaxial cables 700b. In the exemplary embodiment disclosed, solder mass 810 is positioned between the first row of coaxial cables 700a and the second row of coaxial cables 700b. Solder mass 810 is also positioned between each coaxial cable within first set of coaxial cables 700a and between each coaxial cable within second set of coaxial cables 700b. Solder mass 810 is also positioned between first set of coaxial cables 700a and grounding pad 430.

Referring again to FIG. 5, method 500 describes mechanically and electrically bonding center conductors 720a to conductive pads 602 before mechanically and electrically bonding shield layers 710a to grounding pad 430 in steps 515 and 520. Similarly, method 500 describes mechanically and electrically bonding center conductors 720b to conductive pads 604 before mechanically and electrically bonding shield layers 710b to grounding pad 430 in steps 530 and 535. However, this particular order of connecting center conductors 720a or 720b of coaxial cables 700a or 700b before connecting shield layers 710a or 710b to grounding pad 430 is not required. Shield layers 710a or 710b may be mechanically and electrically bonded to grounding pad 430 before center conductors 720a or 720b are bonded to conductive pads 602 or 604.

Figure 10A:
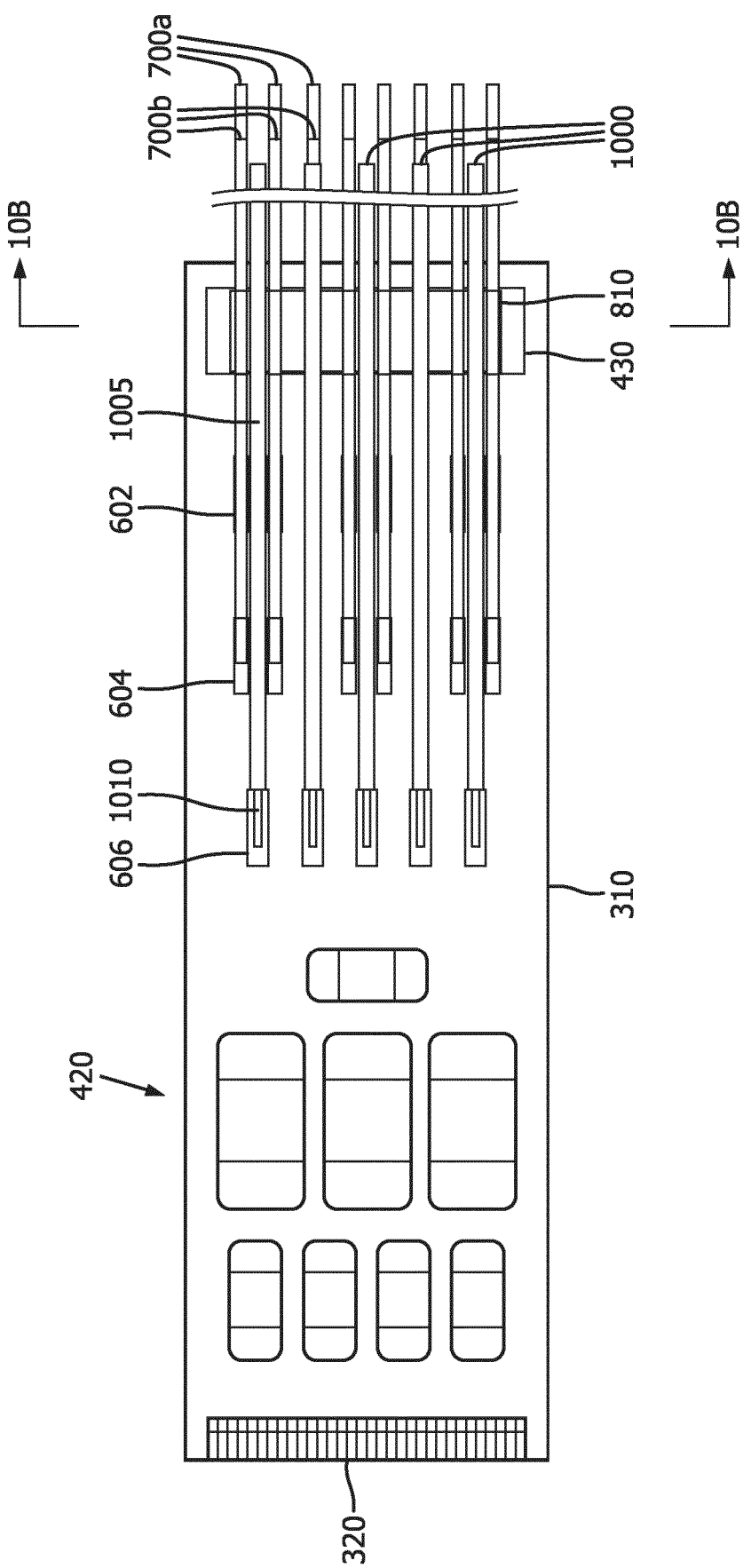
FIG. 10A is a top view of the interposer of FIG. 6A with first and second rows of coaxial cables connected, and a third top row of center conductor cables positioned above coaxial cables according to an embodiment of the present disclosure.

Referring again to FIG. 5, at step 540, method 500 includes obtaining a set of single conductor cables 1000. Single conductor cables 1000 may be substantially similar to single conductor cables well known to those skilled in the art. FIG. 10A shows a third set of five such single conductor cables positioned over first set of coaxial cables 700a and second set of coaxial cables 700b. In some embodiments, single conductor cables 1000 are primarily composed of two layers. It is contemplated, however, that additional layers may be added in other embodiments of the present invention which provide additional functionality. For example, layers that provide additional strength, rigidity, protection, increased conductivity, or any other function may be added to single conductor cables 1000. As shown in FIG. 10A, a single conductor 1010 extends along the inside of single conductor cables 1000. Single conductor 1010 may be used to transmit signals from the control and processing system 130 to the ultrasound imaging assembly 102 or from the ultrasound imaging assembly 102 to the control and processing system 130. For example, the single conductor 1010 can be a power line or thermistor sensing lead. In such embodiments, the single conductor 1010 can carry power signals or thermistor signals. The single conductor 1010 may be used for any number of other suitable applications as well.

Disposed around single conductor 1010 is an insulation layer 1005. Insulation layer 1005 extends primarily from the proximal to distal ends of single conductor 1010. A purpose of insulation layer 1005 may be to insulate single conductor 1010 from the general environment and ensure that single conductor 1010 is only in electrical communication with the control and processing system 130 and the ultrasound imaging assembly 102 as may be intended. Insulation layer 1005 is removed to expose a distal portion of single conductor 1010 as shown in FIG. 10A. Single conductor cables 1000 may be obtained in such a way as to expose the distal portion of single conductor 1010 or single conductor cables 1000 may alternatively be modified after obtaining cables 1000 such that single conductor 1010 is exposed as shown. Although the present disclosure depicts only two layers comprising single conductor cables 1000, many additional layers serving different functions may be included in single conductor cables 1000 as previously mentioned.

Referring again to FIG. 5, at step 545, method 500 includes mechanically and electrically coupling single conductor cables 1000 to conductive pads 606 such that single conductor cables 1000 are positioned above first set of coaxial cables 700a and second set of coaxial cables 700b. As shown in FIG. 10A, single conductor cables 1000 are substantially similar to one another. FIG. 10A depicts five such single conductor cables 1000 positioned on interposer 310, however, it is fully contemplated that any number of single conductor cables 1000 may be included in this set. Single conductor cables 1000 may include only one single conductor cable 1000, two, four, eight, 16, hundreds or more of single conductor cables 1000.

Figure 10B:
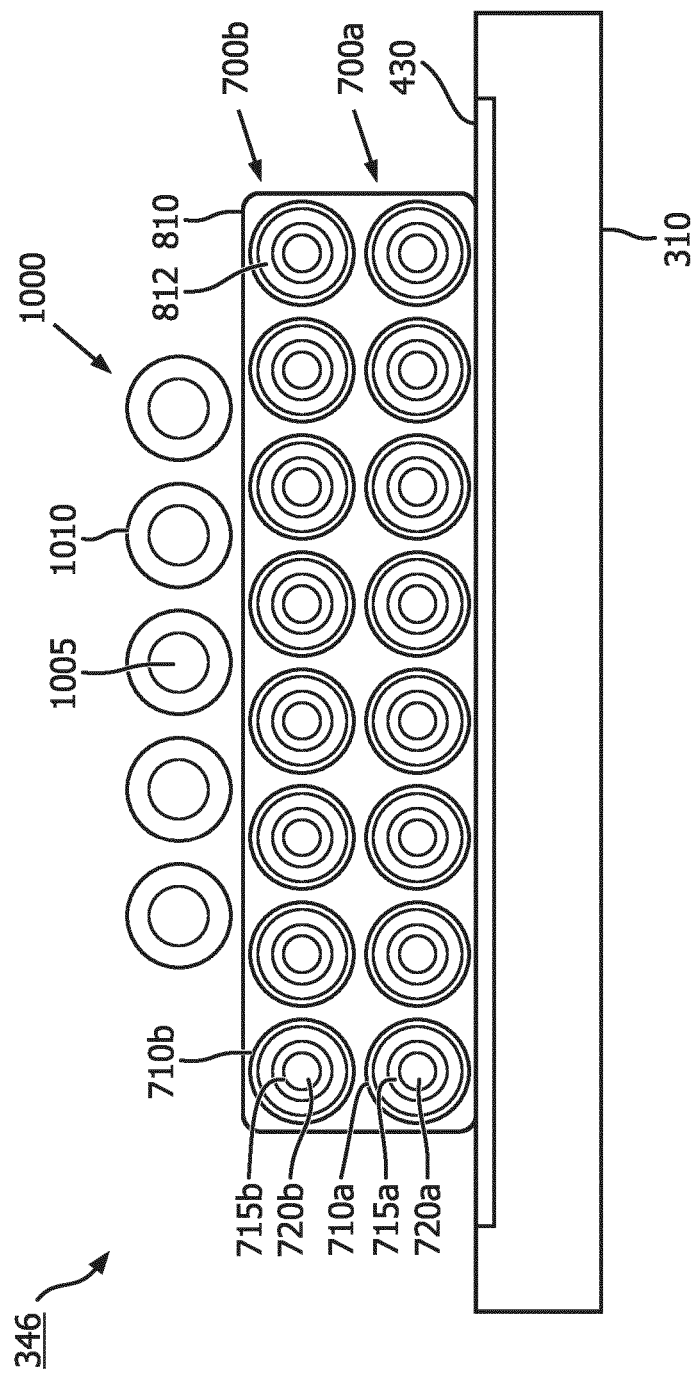
FIG. 10B is a cross-sectional view of an interposer with first and second rows of coaxial cables connected, and a third top row of center conductor cables positioned above coaxial cables according to an embodiment of the present disclosure.

As shown in FIG. 10A, single conductor 1010 of each single conductor cable 1000 is mechanically and electrically bonded to a corresponding conductive pad 606 positioned on interposer 310. Because five single conductor cables 1000 are shown in FIG. 10A, interposer 310 shows five corresponding conductive pads 606 positioned near conductive pads 604. As mentioned, this number is merely illustrative. In some embodiments, conductive pads 602 are positioned between conductive pads 604 and grounding pad 430, and conductive pads 604 are positioned between conductive pads 606 and conductive pads 602. This orientation allows the second set of coaxial cables 700b to be positioned over the first set of coaxial cables 700a, and the single conductor cables 1000 to be positioned over both first set of coaxial cables 700a and second set of coaxial cables 700b as to create two rows of coaxial cables 700a and 700b and one row of single conductor cables 1000 as shown in FIG. 10B. However, conductor pads 602, 604, and 606 may be positioned at any place on interposer 310. A mechanical and electrical bond between single conductors 1010 and grounding pads 606 may be achieved by any suitable method, including but not limited to the use of solder, adhesive, insulating tape, wire gel connectors, grease filled connectors, rubber welding, heat shrinking, or any other suitable form of mechanical and electrical connection. It is also contemplated that single conductor cables 1000 need not be positioned above first set of coaxial cables 700a and second set of coaxial cables 700b. They may be positioned to either side of or beneath the coaxial cables in any suitable manner. It is noted that solder mass 810 which encapsulates first set of coaxial cables 700a and second set of coaxial cables 700b does not encapsulate single conductor cables 1000. Because insulation layer 1005 extends all along single conductor 1010 except near the distal end of single conductor 1010 where it is bonded to conductive pad 606, the solder of solder mass 810 does not wick to single conductor cables 1000.

Referring again to FIG. 10A, the proximal portions of first set of coaxial cables 700a, second set of coaxial cables 700b, and single conductor cables 1000 are depicted as being offset from one another, such that second set of coaxial cables 700b appear to terminate at some location distal to the proximal termination of first set of coaxial cables 700a and single conductor cables 1000 appear to terminate at some location distal to the proximal termination of second set of coaxial cables 700b. Although this orientation may be utilized in an embodiment of the present disclosure, this staggering of the proximal termination of coaxial cables is depicted for primarily pedagogical purposes similar to the staggering of first set of coaxial cables 700a and second set of coaxial cables 700b as described in relation to FIG. 9A. FIG. 10A illustrates the presently disclosed apparatus after all previously mentioned coaxial and single conductor cables have been connected to interposer 310.

FIG. 10B is a cross-sectional view of an interposer 310 along section line 10B-10B in FIG. 10A, with first row of coaxial cables 700a and second row of coaxial cables 700b connected and a third top row of center conductor cables 1000 positioned above first row of coaxial cables 700a and second row of coaxial cables 700b according to an embodiment of the present disclosure. Solder mass 810 envelopes first row of coaxial cables 700a and second row of coaxial cables 700b and mechanically and electrically couples them to grounding pad 430. As previously mentioned, each coaxial cable within first set of coaxial cables 700a comprises center conductor 720a, insulation layer 715a, and shield layer 710a. Similarly, each coaxial cable within second set of coaxial cables 700b comprises center conductor 720b, insulation layer 715b, and shield layer 710b. Solder 812 which may be a portion of or substantially similar to solder mass 810 may be positioned between insulation layer 715a and shield layer 710a for first set of coaxial cables 700a and between insulation layer 715b and shield layer 710b for second set of coaxial cables 700b. As previously mentioned, single conductor cables 1000 each comprise a single conductor 1005 and an insulation layer 1010. It is also noted that cables 346 as shown in FIG. 3B are arranged in a circular manner within the catheter cable 203. At a point proximal to the proximal portion 620 of interposer 310, cables 346 being to transition their arrangement into the three or more rows as shown in FIG. 10B. FIG. 10B illustrates the presently disclosed apparatus after all previously mentioned coaxial and single conductor cables have been connected to interposer 310. In some embodiments, the length and/or width of the solder mass 810 can be equal to the length 432 and/or width 434, respectively, of the grounding pad 430. In some embodiments, the length and/or width of the solder mass 810 can be less than the length 432 and/or width 434, respectively, of the grounding pad 430. The height of the solder mass 810 can depend on the volume of solder that is used to couple the ground padding 430, the first set of coaxial cables 700a, and the second set of coaxial cables 700b.

Figure 11:
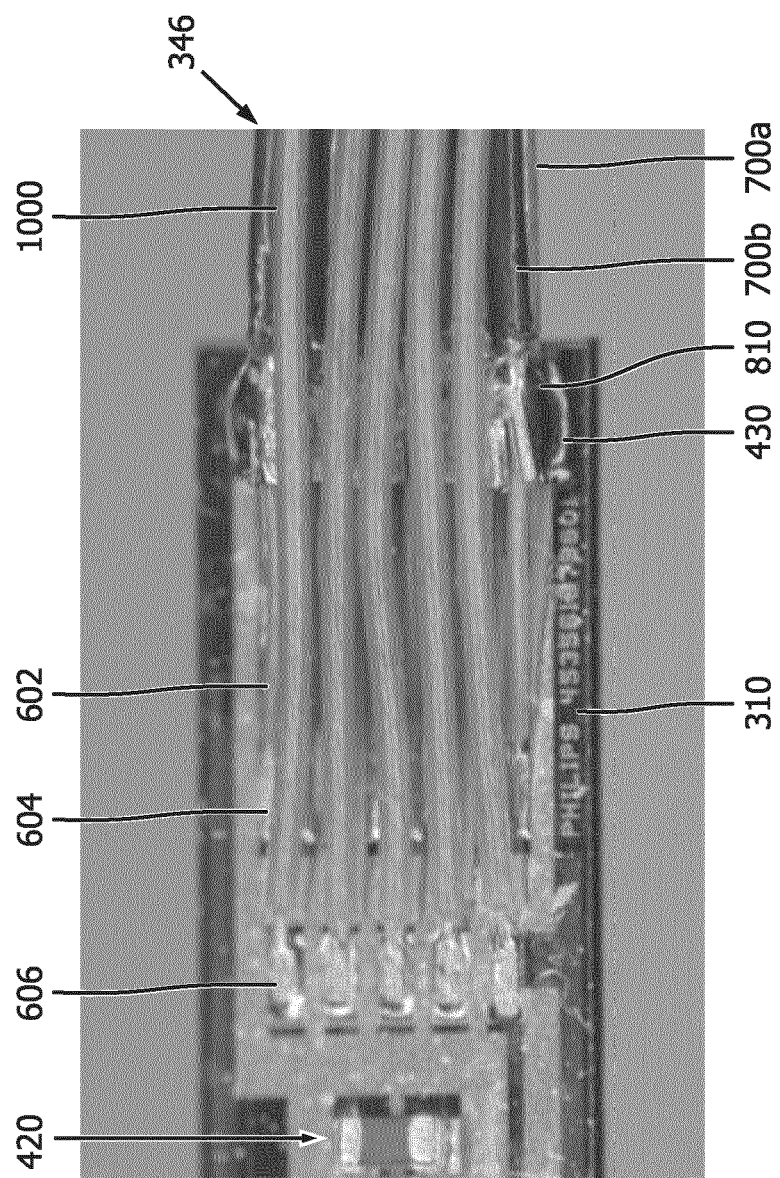
FIG. 11 is a perspective view of an interposer with first and second rows of coaxial cables connected, and a third top row of center conductor cables positioned above coaxial cables according to an embodiment of the present disclosure.

FIG. 11 is a perspective view of an interposer 310 with catheter cables 346 comprising first set of coaxial cables 700a, second set of coaxial cables 700b, and third set of single conductor cables 1000, mechanically and electrically coupled to corresponding conductive pads 602, 604, and 606 and grounding pad 430. Solder mass 810 mechanically and electrically couples first set of coaxial cables 700a and second set of coaxial cables 700b to grounding pad 430. Electrical components 420 may be positioned distally to grounding pads 602, 604, and 606. FIG. 11 illustrates the presently disclosed apparatus after all previously mentioned coaxial and single conductor cables have been connected to interposer 310.

It is noted that although the figures and associated description of the present disclosure depict three sets of cables 346, a first set of coaxial cables 700a, a second cables of coaxial cables 700b, and a set of single conductor cables 1000 arranged in three rows, any number of sets of cables may be used. For example, only one set arranged in one row may be used and mechanically and electrically bonded to interposer 310 according to the embodiments of the present disclosure. Additionally, two, four, five, ten, or more sets of cables may be mechanically and electrically bonded to interposer 310 according to the present disclosure. Additionally, single conductor cables 1000 may be positioned in the same row or set as first set of coaxial cables 700a or second set of coaxial cables 700b. Single conductor cables may be in the same row or set as any other type of cable used in the present disclosure.

Figure 12:
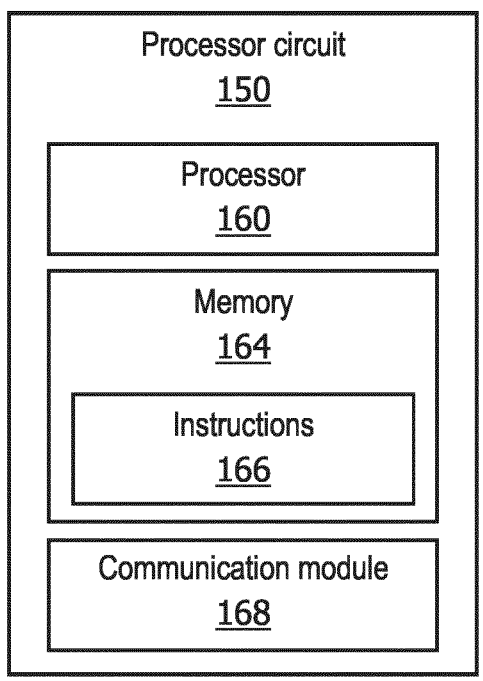
FIG. 12 is a schematic diagram of a processor circuit, according to an embodiment of the present disclosure.

FIG. 12 is a schematic diagram of a processor circuit 150, according to embodiments of the present disclosure. The processor circuit 150 may be implemented in the intraluminal ultrasound imaging device 110, the control and processing system 130, and/or the PIM 131 of FIG. 1A. As shown, the processor circuit 150 may include a processor 160, a memory 164, and a communication module 168. These elements may be in direct or indirect communication with each other, for example via one or more buses.

The processor 160 may include a central processing unit (CPU), a digital signal processor (DSP), an ASIC, a controller, an FPGA, another hardware device, a firmware device, or any combination thereof configured to perform the operations described herein. The processor 160 may also be implemented as a combination of computing devices, e.g., a combination of a DSP and a microprocessor, a plurality of microprocessors, one or more microprocessors in conjunction with a DSP core, or any other such configuration.

The memory 164 may include a cache memory (e.g., a cache memory of the processor 160), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 164 includes a non-transitory computer-readable medium. The memory 164 may store instructions 166. The instructions 166 may include instructions that, when executed by the processor 160, cause the processor 160 to perform the operations described herein with reference to the intraluminal ultrasound imaging device 110, the control and processing system 130, and/or the PIM 131 (FIG. 1A). Instructions 166 may also be referred to as code. The terms "instructions" and "code" should be interpreted broadly to include any type of computer-readable statement(s). For example, the terms "instructions" and "code" may refer to one or more programs, routines, sub-routines, functions, procedures, etc. "Instructions" and "code" may include a single computer-readable statement or many computer-readable statements.

The communication module 168 can include any electronic circuitry and/or logic circuitry to facilitate direct or indirect communication of data between the intraluminal ultrasound imaging device 110, the control and processing system 130 (including the monitor 132 and the control interface 134), and/or the PIM 131. In that regard, the communication module 168 can be an input/output (I/O) device. In some instances, the communication module 168 facilitates direct or indirect communication between various elements of the processor circuit 150 and/or the system 100.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal imaging device, comprising:
   a handle;
   a flexible elongate member coupled to the handle, wherein the handle is configured to be manipulated by a user for manual control of the flexible elongate member within a body lumen of a patient, wherein the flexible elongate member comprises a plurality of coaxial cables, wherein each of the plurality of coaxial cables comprises a conductive shield layer; and
   an ultrasound imaging assembly positioned at a distal portion of the flexible elongate member and in communication with the plurality of coaxial cables, the ultrasound imaging assembly comprising:
     a transducer array configured to obtain ultrasound data;
     a first conductive pad; and
     a single solder mass positioned over the first conductive pad, wherein the single solder mass contacts and extends between the conductive shield layers of each of the plurality of coaxial cables, wherein the conductive shield layer of each of the plurality of coaxial cables is mechanically and electrically coupled to the first conductive pad and to each other by the single solder mass such that the single solder mass is configured to support a tensile pull load of at least 15 N occurring while the flexible elongate member is under the manual control.

2. The intraluminal imaging device of claim 1, wherein the single solder mass is positioned around a perimeter of the plurality of coaxial cables.

3. The intraluminal imaging device of claim 1,
   wherein each of the plurality of coaxial cables comprises an insulating jacket around the conductive shield layer,
   wherein the conductive shield layer comprises an exposed portion without the insulating jacket, and
   wherein corresponding dimensions of the exposed portion of the conductive shield layer and the first conductive pad are equal.

4. The intraluminal imaging device of claim 1, wherein each of the plurality of coaxial cables is spaced apart, wherein the single solder mass is positioned between each of the plurality of coaxial cables.

5. The intraluminal imaging device of claim 1, wherein the first conductive pad comprises an electrical ground for the plurality of coaxial cables.

6. The intraluminal imaging device of claim 1, wherein the flexible elongate member comprises a catheter configured to be positioned within a heart of the patient.

7. The intraluminal imaging device of claim 1, wherein the ultrasound imaging assembly further comprises a circuit board in communication with the transducer array, the first conductive pad positioned on a surface of the circuit board.

8. The intraluminal imaging device of claim 1, wherein the conductive shield layer is at least semi-porous such that the single solder mass passes through the conductive shield layer.

9. The intraluminal imaging device of claim 1, wherein the single solder mass is positioned between the conductive shield layer of each of the plurality of coaxial cables.

10. The intraluminal imaging device of claim 1,
    wherein each of the plurality of coaxial cables comprises a center conductor and an insulation layer around the center conductor, wherein the conductive shield layer is positioned around the insulation layer, and wherein the single solder mass is positioned between the conductive shield layer and the insulation layer.

11. The intraluminal imaging device of claim 10, wherein the single solder mass extends through the conductive shield layer.

12. The intraluminal imaging device of claim 1, wherein the plurality of coaxial cables comprises a first row of coaxial cables and a second row of coaxial cables, wherein the first row of coaxial cables is positioned over the first conductive pad, and wherein the second row is positioned over the first row of coaxial cables.

13. The intraluminal imaging device of claim 12, wherein the single solder mass is positioned between the first row of coaxial cables and the second row of coaxial cables.

14. The intraluminal imaging device of claim 1, wherein each of the plurality of coaxial cables comprises a center conductor, wherein the ultrasound imaging assembly comprises a plurality of second conductive pads, wherein the center conductor of each of the plurality of coaxial cables is mechanically and electrically coupled to a corresponding one of the plurality of second conductive pads, and wherein the center conductor is configured to carry electrical signals to and from the ultrasound imaging assembly.

15. The intraluminal imaging device of claim 14, wherein the flexible elongate member comprises a plurality of single conductor cables positioned over the plurality of coaxial cables, wherein the ultrasound imaging assembly comprises a plurality of third conductive pads configured to be mechanically and electrically coupled to the plurality of single conductor cables, and wherein the plurality of single conductor cables are configured to carry the electrical signals to and from the ultrasound imaging assembly.

16. A system, comprising:

an intraluminal imaging device, comprising:

a handle;

a flexible elongate member coupled to the handle, wherein the handle is configured to be manipulated by a user for manual control of the flexible elongate member within a body lumen of a patient, wherein the flexible elongate member comprises a plurality of coaxial cables, wherein each of the plurality of coaxial cables comprises a conductive shield layer; and an ultrasound imaging assembly positioned at a distal portion of the flexible elongate member and in communication with the plurality of coaxial cables, the ultrasound imaging assembly comprising:

a transducer array configured to obtain ultrasound data;

a conductive pad; and a single solder mass positioned over the conductive pad, wherein the single solder mass contacts and extends between the conductive shield layers of each of the plurality of coaxial cables, wherein the conductive shield layer of each of the plurality of coaxial cables is mechanically and electrically coupled to the conductive pad and to each other by the single solder mass such that the single solder mass is configured to support a tensile pull load of at least 15 N occurring while the flexible elongate member is under the manual control; and a computer in communication with the intraluminal imaging device and configured to generate an ultrasound image based on the ultrasound data.

* * * * *